United States Patent
Obata et al.

(10) Patent No.: US 6,410,280 B1
(45) Date of Patent: Jun. 25, 2002

(54) DECAPRENYL DIPHOSPHATE SYNTHETASE GENE

(75) Inventors: Shusei Obata, Aichi; Tokuzo Nishino; Tanetoshi Koyama, both of Miyagi; Yoshihiro Sato, Aichi, all of (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/808,126

(22) Filed: Mar. 15, 2001

Related U.S. Application Data

(62) Division of application No. 09/025,819, filed on Feb. 19, 1998, now Pat. No. 6,225,097.

(30) Foreign Application Priority Data

Sep. 17, 1997 (JP) .............................................. 9-251675

(51) Int. Cl.[7] .................................................. C12P 7/66
(52) U.S. Cl. .................... 435/133; 435/232; 435/252.3; 435/252.33; 435/320.1; 536/23.2
(58) Field of Search ................................ 435/133, 232, 435/252.3, 252.33, 23.2, 320.1; 536/23.2

(56) References Cited

FOREIGN PATENT DOCUMENTS

EP          88113948.9          8/1988

OTHER PUBLICATIONS

Saiki, Randall K. et al., "Primer–Directed Enzymatic Amplification of DNA with a Thermostable DNA Polymerase", *Science*, pp. 487–491 (1989).
Guatelli, John C. et al., "Isothermal, in Vitro Amplification of Nucleic Acids by a Multienzyme Reaction Modeled After Retroviral Replication", *Proc. Natl. Acad. Sci. USA*, vol. 87, pp. 1874–1878 (1990).
Compton, J., "Nucleic Acid Sequence–Based Amplification", *Nature*, vol. 350, pp. 91–92 (1991).
Walker, G. Terrance et al., "Strand Displacement Amplification—An Isothermal, in vitro DNA Amplification Technique", *Nucleic Acids Research*, vol. 20, No. 7, pp. 1691–1696 (1992).
Abe, Chiyoji et al., "Detection of *Mycobacterium tuberculosis* in Clinical Specimens by Polymerase Chain Reaction and Gen–Probe Amplified Mycobacterium Tuberculosis Direct Test", *Journal of Clinical Microbiology*, vol. 31, No. 12, pp. 3270–3274 (1993).
Mueller, James D. et al., "Self–Sustained Sequence Replication (3SR): An Alternative to PCR", *Histochem Cell Biol*, 108:431–437 (1997).
Suzuki, Kengo et al., "Isolation of Decaprenyl Disphosphate Synthase (DPS) Gene from Fission Yeast *S. pombe* And Characteristics of Deletion Mutant Lacking The Gene", *The Japanese Biochemical Society/The Molecular Biology Society of Japan*, 2–P–0156, p. 230, Jul. 25, 1996.

Okada, Yasunori et al., "Isolation of Decaprenyl Disphosphate Synthase (DDS) Gene from Acetic Acid Bacterium *Gluconobacter suboxydans* And Expression of the Gene", *The Japanese Biochemical Society/The Molecular Biology Society of Japan*, 2–P–0157, p. 230, Jul. 25, 1996.
Eberhardt et al., *J. Biol. Chem.*, 250:3, pp 863–866, Feb. 10, 1975.
Sagami et al., *J. Biol. Chem.*, 269:32, pp 20561–20566, Aug. 12, 1994.
Fujii et al., *Biochemica et Biophysica Acta*, 712:716–718, 1982.
Takahashi et al., *J. Biol. Chem.*, 255;10, pp 4539–4543, May 25, 1980.
Ohnuma et al., *J. Biol. Chem.*, 266:35, pp 23706–23713, Dec. 15, 1991.
John et al., *Nature*, 254, pp 495–498, Apr. 10, 1975.
Ishii et al., *Biochem. J.*, 233, pp 773–777, 1986.
Ishii et al., *Biochem & Biophys. Res. Comm.*, 116:2, pp 500–506, Oct 31, 1983.
Fujioka et al., *Tohuku J. Exp. Med.*, 141, Suppl. pp 453–463, 1983.
Koyama et al., *J. Biochem.*, 113:3, pp 355–363, 1993.
Saito et al., *Biochimica et Biophysica Acta*, 72, pp 619–629, 1963.
Construction of Genomic Libraries, "Molecular Cloning", pp 269–307, 1982.
Nelson et al., *Methods in Enzymology*, 68:41–51, 1979.
Koike–Takeshita et al., *J. Biol. Chem.*, 270:31, pp 18396–18400, Aug. 4, 1995.
Jeong et al., *J. DNA Sequencing and Mapping*, 4:59–67, 1993.
Sanger et al., *Proc. Natl. Acad. Sci. USA*, 74:12, pp 5463–5467, Dec. 1977.
Kunkel, *Proc. Natl. Acad. Sci. USA*, 82:488–492, Jan. 1985.
Hanahan, *J. Mol. Biol.*, 166–557–580, 1983.
Becker et al., *Methods in Enzymology*, 194:182–187, 1991.
Hinnen et al., *Proc. Natl. Acad. Sci. USA*, 75:4, pp 1929–1933, Apr. 1978.
Ito et al., *J. of Bacteriology*, 153:1, pp 163–168, Jan. 1983.
Yabutani et al., *FEMS Microbiology Letters*, 133:85–90, 1995.
Barnes, *Proc. Natl. Acad. Sci. USA*, 91:2216–2220, Mar. 1994.
Amann, *Gene*, 69:2, pp 301–315, 1988.
Fujii et al., *J. of Biol. Chem.*, 257:24, pp 14610–14612, Dec. 25, 1982.

Primary Examiner—Nashaat T. Nashed
(74) Attorney, Agent, or Firm—Kenyon & Kenyon

(57) ABSTRACT

The present invention provides a prenyl diphosphate synthetase and a gene coding for the synthetase. The invention discloses a recombinant protein having the amino acid sequence shown in SEQ ID NO:2 or a recombinant protein which has the amino acid sequence shown in SEQ ID NO:2 having deletion, substitution or addition of at least one amino acid and which has decaprenyl diphosphate synthetase activity; a gene coding for the protein; a recombinant vector comprising the gene; a transformant transformed with the vector; a method for producing a decaprenyl diphosphate synthetase; and a method for producing ubiquinone-10.

6 Claims, 17 Drawing Sheets

Biosynthesis of Isoprenoids

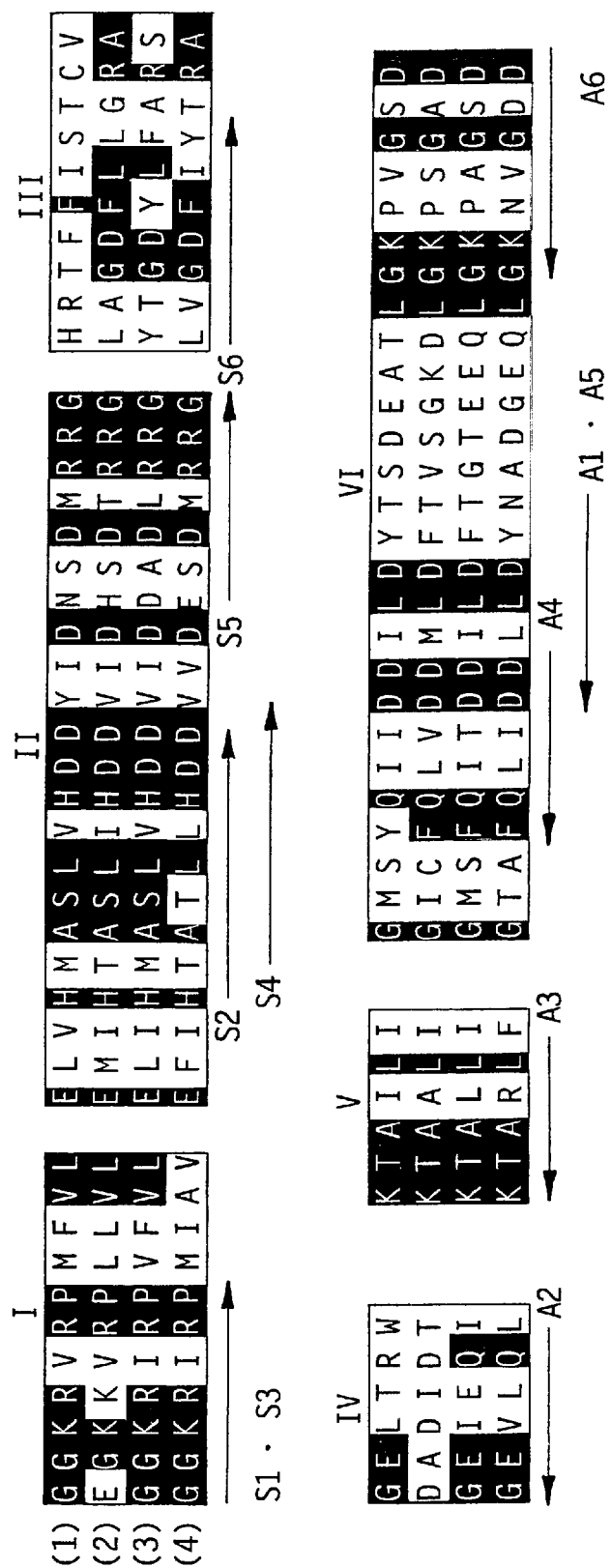

FIG. 3

(1) Hexaprenyl diposhate (HexPP) synthetase from Micrococcus luteus B-P26
(2) Hexaprenyl diposhate (HexPP) synthetase from Saccharomyces cerevisiae
(3) Heptaprenyl diphosphate (HepPP) synthetase from Bacillus stearothermophilus
(4) Octaprenyl diphosphate (OctPP) synthetase from Escherichia coli Design of PCR Primers based on the Amino Acid Sequences of the Preserved Regions

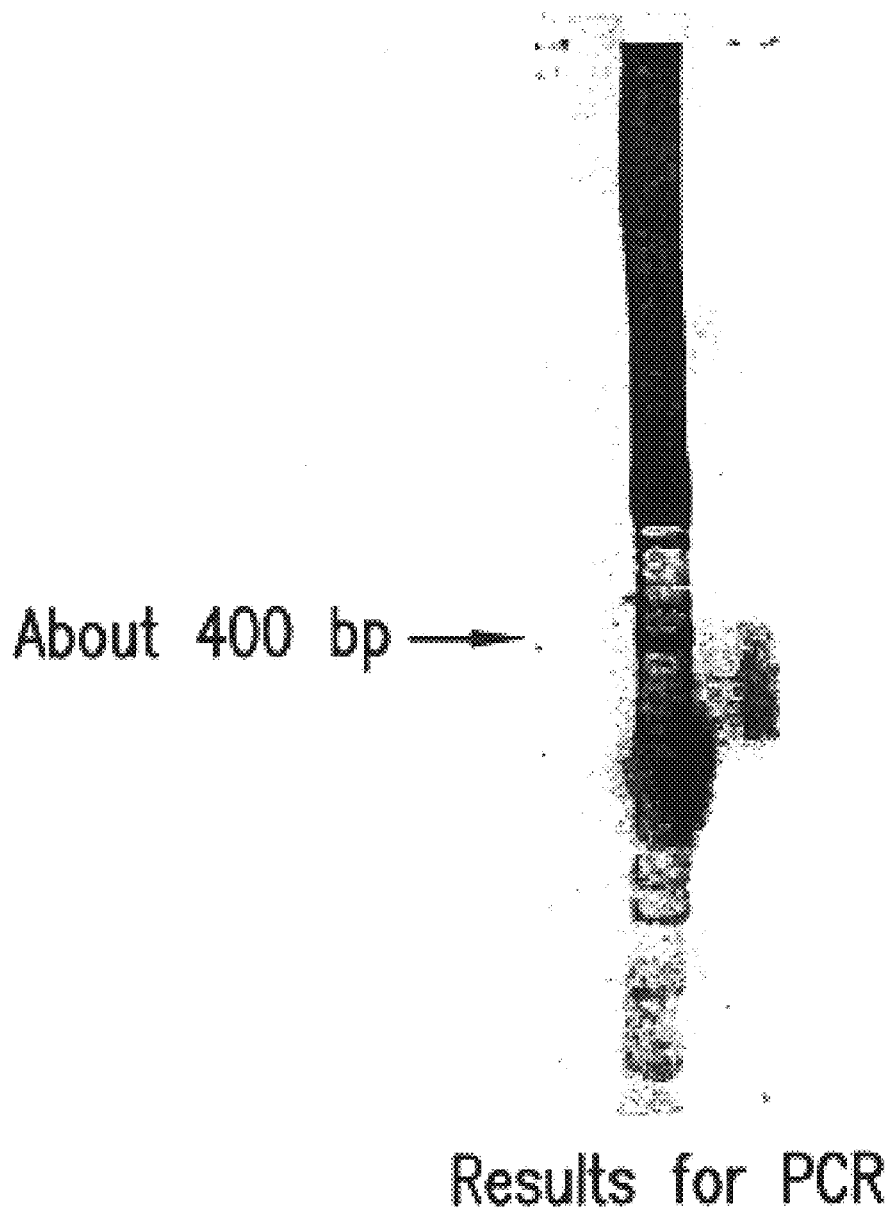

[45.7% / 138 aa]

(1) 1'                         VVDESQQRRGRPTANLLWDNKSSVLVGDYLFARSF
                               ***.*.***..*.******....*.*
(2) 61" YEGNAHVTIAALIEFIHTATLLHDDVVDESDMRRGKATANAAFGNAASVLVGDFIYTRAF (1) 36' QLMADTESMQVMRILANASATIAEGEVLQLTAAQDVSTTEDTYIQIVRGKTAALFSAATE
        *.*...*.*.....*..********...*..**..*.....*..**..
(2) 121" QMMTSLGSLKNLEVMSEAVNVIAEGEVLQLMNVNDPDITEENYMRVIYSKTARLFEAAAQ (1) 96' AGAVVAGGAPAVQQALFDYGDALGIPFQIVDDLLDYGGSTTTI
        ....**.*....*....****......
(2) 181" CSGILAGCTPEEEKGLQDYGRYLGTAFQLIDDLLDYNADGEQLGKNVGDDLNEGKPTLPL (1) pCR 14
    (2) OctPP Synthetase from E. coli Comparison between the Deduced Amino Acid Sequence for the Base Sequence for pCR14 and the Amino Acid Sequence for OctPP Synthetase

FIG. 5

Design of BS and BA primers

FIG. 7B

Moderate conditions
1  2  3

23.0 —
9.4 —
6.6 —
4.4 —

2.3 —
2.0 —

1 P. denitrificans chromosomal / ApaI
2 P. denitrificans chromosomal / EcoRI
3 P. denitrificans chromosomal / BamHI Southern Hybridization using a PCR Product as a Probe

FIG. 7A

Stringent conditions
1  2  3

23.0 —
9.4 —
6.6 —
4.4 —

2.3 —
2.0 —

1 P. denitrificans chromosomal / ApaI
2 P. denitrificans chromosomal / EcoRI
3 P. denitrificans chromosomal / BamHI Southern Hybridization using a PCR Product as a Probe Confirmation Of Clones recovered from Positive Colonies by PCR ORF contained in p11A1

```
GATCCCCTCGGCCGCCAGCAGGTGGGCCGGCGCCGGGTGATGAGAAGCGGTCGGTGCCGCAGAAGCTCTTTCATGACATGGGAAAGTTA  90
CGCGGCTGTTGCGCCATGTGTCCATGGCGTGGCAATGGCTGGGCGCGGGGCCAAAGGGGATCGCTGATGGGCATGAACGAAAACGTCTCCAAGCCG 180
 R  G  C  C  A  C  V  H  G  V  A  A  G  G  E  R  G  S  L  M  G  M  N  E  N  V  S  K  P
CTCGACCGGCTCTCCGTGAAACTGGCCGGCGGGGATATGGACCGGGTCAATGCCCTGATCCGCGAGCGCATGGCCAGCCGCCACGCCCCCCGC 270
 L  D  R  L  S  V  E  L  A  G  D  M  D  R  V  N  A  L  I  R  E  R  M  A  S  R  H  A  P  R
ATTCCGGAAGTGACCGCGCATCTGGTCGAGGCCGGCGGCAAGCGGCTGCGCCCGATGCTGGTGCTGGCGGCGGCGCGCCTGTGCGGCTAT 360
 I  P  E  V  T  A  H  L  V  E  A  G  G  K  R  L  R  P  M  L  V  L  A  A  A  R  L  C  G  Y
CAGGGGAACAGCCATGTGCTGCTGGCCGCGGCGGTCGAGTTCATCCATACGCCGACGCTTCTGCACGACGTGGTCGATGAAAGCCAG 450
 Q  G  N  S  H  V  L  L  A  A  A  V  E  F  I  H  T  A  T  L  L  H  D  D  V  V  D  E  S  Q
CAGCGGCGCGCGCCGGACGATACGGCCAACCTTCTGTGGGACAACAAGTCCAGTCTGGTCGGCGACTACCTGTTCGCGCAGCTTCCAG 540
 Q  R  R  G  R  P  T  A  N  L  L  W  D  N  K  S  S  V  L  V  G  D  Y  L  F  A  R  S  F  Q
CTGATGGCCGATACGGAAAGCATGCAGGTTCAGGTCATGCGCATCTTGGCCAATGCCAGCCACATCGCCGAGGGCGAGGTGCTGCAGCTGACC 630
 L  M  A  D  T  E  S  M  Q  V  M  R  I  L  A  N  A  S  A  T  I  A  E  G  E  V  L  Q  L  T
GCCCGGCAGGACGTCTCCACCGAGGACACGTACTATCAGATCGTGCGGCAAGACAGCGGCCTGTTTCCGGCCACCGAGGCG 720
 A  Q  D  V  S  T  E  D  T  Y  Y  Q  I  V  R  G  K  T  A  A  L  F  S  A  A  T  E  A
GCGCGGGTGGTCGCCGGCGCCGACCCGGCCGTGCAGCCGGCCCTGTTCGACTATGGCGATGCCCTGGGGATCGCCTTCCAGATCGTGGAC 810
 A  A  V  V  A  G  A  D  P  A  V  Q  Q  A  L  F  D  Y  G  D  A  L  G  I  A  F  Q  I  V  D
GACCTGCTGGATTACGGCGGCAGCACGACCACGGGCAAGAACGTCGGCGACGATTTCCGGGAGCGCAAGCTGACGCTGCCGGTGATC 900
 D  L  L  D  Y  G  G  S  T  T  T  I  G  K  N  V  G  D  D  F  R  E  R  K  L  T  L  P  V  I
AAGGCCCATCGCCGCGGCGACGAGGCCGAGGCCCGCGCCTTCTGGGAACGCACCATCGGCCAGGGCAGGCAGGACGAGGCCGACCTGGCCACC 990
 K  A  I  A  R  A  D  E  A  E  R  A  F  W  E  R  T  I  G  Q  G  R  Q  D  E  A  D  L  A  T
GCGCTGGAGATCCTGCGCCGCCGGGAGGCGCTGGAGGCCCGCGCCGATGCCATCGCCTGGGCCCGCGCCAAGGCGCTGCAA 1080
 A  L  E  I  L  R  R  R  E  A  L  E  A  A  R  A  D  A  I  A  W  A  G  R  A  K  A  A  L  Q
GCCGCGCCGACCAGCCGCTGCGCCGCCTGGCCGGACCTGGCGGATTTCGTGGTCTCGCGCCTGTCTGACCAAAGCCCCCGCACAAA 1170
 A  A  P  D  Q  P  L  R  R  I  L  A  D  L  A  D  F  V  V  S  R  L  S  *
TGAAAAAGCCCGGCGCCATGTGCCGGGCTTTTCCTTTGCCTGAAGCGCTG
```

* Underlined portion is identical with the sequence of pCR14
* Boxed portions seem to be SD sequences.

FIG. 11

Comparison with Various Prenyltransferases

```
                                                                       I
(1)  1:-------------------------------MDFPQQLEACVKQANQALSRFIAPLPFQNTPVVETMQYGALLGGKRL  47
(2)  1:-------------------------------MAQLSV-EQELNEQKQAVETALSRYIERLEGPAKLKKAMAYSLAEGGKRI  49
(3)  1:-------------------------------MTVCAKKHVHLTRDAAEQLLADIDRRLDQLLPVEGERDVVGAAMREGALAPGKRI  55
(4)  1:-------------------------------MIALSYKAFLNPYIIEVEKRLYECIQSDSETINKAAHHILSSGGKRV  47
(5)  1:-------------------------------MKLKAMYSFLSDDLAAVEEELERAVQSEYGPLGEAALHLLQAGGKRI  47
(6)  1:-------------------------------MNLEKINELTAQDMAGVNAAILEQLNSDVQLINQLGYYIVSGGGKRI  47
(7)  1:MGKLRGCCACVHGVAMAGGERGSLMGMNENVSKPLDRLSVELAGDMDRVNALIRERMASRHAPRIPEVTAHLVEAGGKRL  80
                                                                     ***

II                    III
 48:RPFLVYATGHMFG--VSTNTLDAPAAAVECIHAYSLIHDDLPAMDDDDLRRGLPTCHVKFGEANAILAGDALQTLAFSIL  125
 50:RPLLLLSTVRALG--KDPAVGLPVACAIEMIHTYSLIHDDLPSMDNDDLRRGKPTNHKVFGEAMAILAGDGLLTYAFQLI  127
 56:RPMLLLLTARDLGCAVSHDGLLDLACAVEMVHAASLILDDMPCMDDAKLRRGRPTIHSHYGEHVAILAAVALLSKAFGVI  133
 48:RPMFVLLSGFLND--TQKDDLIRTAVSLELVHMASLVHDDYI---DNSDMRRGNTSVHIAFDKDTAIRTGHFLLARALQNI  123
 48:RPVFVLLAARFGQ--YDLERMKHVAVALELIHMASLVHDDVI---DDADLRRGRPTIKAKWSNRFAMYTGDYLFARSLERM  123
 48:RPMIAVLAARAVG--YEGNAHVTIAALIEFIHTATLLHDDVV--DESDMRRGKATANAAFGNAASVLVGDFIYTRAFQMM  123
 81:RPMLVLAAARLCG--YQGNSHVLLAAAVEFIHTATLLHDDVV--DESQQRRGRPTANLLWDNKSSVLVGDYLFARSFQLM  156
     **                 * * **  *   ***

IV                   V
126:SDADMPEVSDRDRISMISELASASGTAGMCGGQALDLDAEGKHVPLDALERIHRH-KTGALIRAAVRLGALSAGDKGRRA  204
128:TEIDDERIPPSVRLRLIERLAKAAGPEGMVAGQAADMEGEGKTLTLSELEYIHRH-KTGKMLQYSVHAGAL--GGADARQ  204
134:ADADGLTPLAKNRA-VSELSNAIGMQGLVQGQFKDLSEGDKPRSAEAILMTNHF-KTSTLFCASMQMASIVANASSE-A  209
124:ATINNSKFHQIFSK---------TILEVCFGEFDQMADRFNYPVSFTAYLRRINRKTAILIEASCHLGALSSQLDEQ-S  192
124:AELGNPRAHQVLAK---------TIVEVCRGEIEQIKDKYRFDQPLRTYLRRIRRKTALLIAASCQLGALAAGAPEP-I  192
124:TSLGSLKVLEVMSE---------AVNVIAEGEVLQLMNVNDPDITEENYMRVIYSKTARLFEAAAQCSGILAGCTPE-E  192
157:ADTESMQVMRILAN---------ASATIAEGEVLQLTAAQDVSTTEDTYIQIVRGKTAALFSAATEAGAVVAGADPA-V  225
                                                **

VI
205:LPVLDKYAESIGLAFQVQDDILDVVGDTATLGKRQGADQQLGKSTYP--ALLGLEQAR-------------------  260
205:TRELDEFAAHLGLAFQIRDDILDIEGAEEKIGKPVGSDQSNNKATYP--ALLSLAGAK-------------------  260
210:RDCLHRFSLDLGQAFQLLDDLTDGMTDT----GKDSNQD--AGKSTLVNLLGPRAVEEERLR--------------  264
193:TYHIKQFGHCIGMSYQIIDDILDYTSDEATLGKPVGSDIRNGHITYPLMAAIANLKEQDDDKLEAVVKHLTSTSDDEVYQ  272
193:VKRLYWFGHYVGMSFQITDDILDFTGTEEQLGKPAGSDLLQGNVTLPVLYALSDERVKAAIAAVGPETDVAEMAAVISAI  272
193:EKGLQDYGRYLGTAFQLIDDLLDYNADGEQLGKNVGDDLNEGKPTLPLLHAMHHGTPEQAQMIRTAIEQG-NGRHLLEPV  271
226:QQALFDYGDALGIAFQIVDDLLDYGGSTTTIGKNVGDFRERKLLTPVIKAIARADEAERAFWERTIGQGRQDEADLATA  305
      * *  **  *     **   *      *

VII
261:--------------KKARDLIDDARQSLKQLAEQSLDTSALEALADYIIQRNK  299
261:--------------EKLAFHIEAAQRHL-RNA--DVDGAALAYICELVAARDH  296
265:-----------------QHLQLASEHLSAACQHGHATQHFIQAWFDKKLAAVS  300
273:YIVSQVKQYGIEPAELLSRKYGDKAKYHLSQLQDSNIKDY-LEEIHEKMLKRVY  325
273:KRTDAIERSYALSDRYL-----DKALHLLDGLPMNEARGL-LRDLALYIGKRDY  320
272:LEAMNACGSLEWTRQRAEEEA-DKAIAALQVLPDTPWREA-LIGLAHIAVQRDR  323
306:LEILRRREALEAARADAIAWA-GRAKAALQAAPDQPLRRI-LADLADFVVSRLS  357
                        * *
```

(1) FPP synthetase from E. coli
(2) FPP synthetase from B. stearothermophilus
(3) GGPP synthetase from E. uredovora
(4) HexPP synthetase from M. luteus
(5) HepPP synthetase from B. stearothermophilus
(6) OctPP synthetase from E. coli
(7) ORF contained in p11A1

FIG. 12

Structure of Genes Upstream and Downstream of ORF

Confirmation of Enzyme Expression by SDS-PAGE

Analysis of Quinone Side chains by HPLC

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 996 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 1..993

(xi) SEQUENCE DESCRIPTION: SEQ ID NO: 1:

```
ATG GGC ATG AAC GAA AAC GTC TCC AAG CCG C TC GAC CGG CTC TCC GTG        48
Met Gly Met Asn Glu Asn Val Ser Lys Pro L eu Asp Arg Leu Ser Val
 1               5                  10                  15

GAA CTG GCC GGG GAT ATG GAC CGG GTC AAT G CG CTG ATC CGC GAG CGC        96
Glu Leu Ala Gly Asp Met Asp Arg Val Asn A la Leu Ile Arg Glu Arg
                20                  25                  30

ATG GCC AGC CGC CAC GCC CCC CGC ATT CCG G AA GTG ACC GCG CAT CTG       144
Met Ala Ser Arg His Ala Pro Arg Ile Pro G lu Val Thr Ala His Leu
         35                  40                  45

GTC GAG GCC GGC GGC AAG CGG CTG CGG CCG A TG CTG GTG CTG GCG GCG       192
Val Glu Ala Gly Gly Lys Arg Leu Arg Pro M et Leu Val Leu Ala Ala
     50                  55                  60

GCG CGG CTG TGC GGC TAT CAG GGG AAC AGC C AT GTG CTG CTG GCC GCG       240
Ala Arg Leu Cys Gly Tyr Gln Gly Asn Ser H is Val Leu Leu Ala Ala
 65                  70                  75                  80

GGG TCG AGT TCA TCC ATA CCG CGA CGC TTC T GC ACG ACG ACG TGG TCG       288
Gly Ser Ser Ser Ser Ile Pro Arg Arg Phe C ys Thr Thr Thr Trp Ser
                85                  90                  95

ATG AAA GCC AGC AGC GGC GCG GCC GGC CGA C GG CCA ACC TTC GTG GGA       336
Met Lys Ala Ser Ser Gly Ala Ala Gly Arg A rg Pro Thr Phe Val Gly
            100                 105                 110

CAA CAA GTC CAG CGT GCT GGT CGG CGA CTA C CT GTT CGC GCG CAG CTT       384
Gln Gln Val Gln Arg Ala Gly Arg Arg Leu P ro Val Arg Ala Gln Leu
        115                 120                 125

CCA GCT GAT GGC GGA TAC GGA AAG CAT GCA G GT CAT GCG CAT CTT GGC       432
Pro Ala Asp Gly Gly Tyr Gly Lys His Ala G ly His Ala His Leu Gly
    130                 135                 140

CAA TGC CAG CGC CAC CAT CGC CGA GGG CGA G GT GCT GCA GCT GAC CGC       480
Gln Cys Gln Arg His His Arg Arg Gly Arg G ly Ala Ala Ala Asp Arg
145                 150                 155                 160

CGC GCA GGA CGT CTC GAC CAC CGA GGA CAC T AT ATC CAG ATC GTG CGC       528
Arg Ala Gly Arg Leu Asp His Arg Gly His T yr Ile Gln Ile Val Arg
                165                 170                 175

GGC AAG ACA GCG GCG CTG TTT TCC GCC GCG A CC GAG GCG GGG GCG GTG       576
Gly Lys Thr Ala Ala Leu Phe Ser Ala Ala T hr Glu Ala Gly Ala Val
            180                 185                 190

GTG GCC GGC GCC GAC CCG GCG GGC AGC AGG C GC TGT TCG ACT ATG GCG       624
Val Ala Gly Ala Asp Pro Ala Gly Ser Arg A rg Cys Ser Thr Met Ala
        195                 200                 205

ATG CGC TGG GGA TCG CCT TCC AGA TCG TGG A CG ACC TGC TGG ATT ACG       672
Met Arg Trp Gly Ser Pro Ser Arg Ser Trp T hr Thr Cys Trp Ile Thr
    210                 215                 220
```

```
GCG GCT CGA CCA CGA CAT CGG CAA GAA CGT C GG CGA CGA TTT CCG CGA    720
Ala Ala Arg Pro Arg His Arg Gln Glu Arg A rg Arg Arg Phe Pro Arg
225                 230                 235                 240

GCG CAA GCT GAC GCT GCC GGT GAT CAA GGC C AT CGC CCG CGC CGA CGA    768
Ala Gln Ala Asp Ala Ala Gly Asp Gln Gly H is Arg Pro Arg Arg Arg
                245                 250                 255

GGC CGA GCG CGC CTT CTG GGA ACG CAC CAT C GG CCA GGG CCG GCA GGA    816
Gly Arg Ala Arg Leu Leu Gly Thr His His A rg Pro Gly Pro Ala Gly
            260                 265                 270

CGA GGC CGA CCT GGC CAC CGC GCT GGA GAT C CT GCG CCG CCG CGA GGC    864
Arg Gly Arg Pro Gly His Arg Ala Gly Asp P ro Ala Pro Pro Arg Gly
        275                 280                 285

GCT GGA GGC CGC CCG CGC CGA TGC GAT CGC C TG GGC CGG CCG TGC CAA    912
Ala Gly Gly Arg Pro Arg Arg Cys Asp Arg L eu Gly Arg Pro Cys Gln
    290                 295                 300

GGC CGC GCT GCA AGC CGC GCC CGA CCA GCC C CT GCG CCG CAT CCG GCG    960
Gly Arg Ala Ala Ser Arg Ala Arg Pro Ala P ro Ala Pro His Pro Ala
305                 310                 315                 320

GAC CTG GCG GAT TTC GTG GTC TCG CGC CTG T CC TGA                    996
Asp Leu Ala Asp Phe Val Val Ser Arg Leu S er
                325                 330

(2) INFORMATION FOR SEQ ID NO: 2:

(i) SEQUENCE CHARACTERISTICS:
        (A) LENGTH: 331 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Met Asn Glu Asn Val Ser Lys Pro L eu Asp Arg Leu Ser Val
 1               5                  10                  15

Glu Leu Ala Gly Asp Met Asp Arg Val Asn A la Leu Ile Arg Glu Arg
                20                  25                  30

Met Ala Ser Arg His Ala Pro Arg Ile Pro G lu Val Thr Ala His Leu
            35                  40                  45

Val Glu Ala Gly Gly Lys Arg Leu Arg Pro M et Leu Val Leu Ala Ala
        50                  55                  60

Ala Arg Leu Cys Gly Tyr Gln Gly Asn Ser H is Val Leu Leu Ala Ala
65                  70                  75                  80

Gly Ser Ser Ser Ile Pro Arg Arg Phe C ys Thr Thr Thr Trp Ser
                85                  90                  95

Met Lys Ala Ser Ser Gly Ala Ala Gly Arg A rg Pro Thr Phe Val Gly
            100                 105                 110

Gln Gln Val Gln Arg Ala Gly Arg Arg Leu P ro Val Arg Ala Gln Leu
        115                 120                 125

Pro Ala Asp Gly Gly Tyr Gly Lys His Ala G ly His Ala His Leu Gly
    130                 135                 140

Gln Cys Gln Arg His His Arg Arg Gly G ly Ala Ala Ala Asp Arg
145                 150                 155                 160

Arg Ala Gly Arg Leu Asp His Arg Gly His T yr Ile Gln Ile Val Arg
                165                 170                 175

Gly Lys Thr Ala Ala Leu Phe Ser Ala Ala T hr Glu Ala Gly Ala Val
            180                 185                 190

Val Ala Gly Ala Asp Pro Ala Gly Ser Arg A rg Cys Ser Thr Met Ala
        195                 200                 205
```

```
Met Arg Trp Gly Ser Pro Ser Arg Ser Trp Thr Thr Cys Trp Ile Thr
    210                 215                 220
Ala Ala Arg Pro Arg His Arg Gln Glu Arg Arg Arg Arg Phe Pro Arg
225                 230                 235                 240
Ala Gln Ala Asp Ala Ala Gly Asp Gln Gly His Arg Pro Arg Arg Arg
                245                 250                 255
Gly Arg Ala Arg Leu Leu Gly Thr His His Arg Pro Gly Pro Ala Gly
            260                 265                 270
Arg Gly Arg Pro Gly His Arg Ala Gly Asp Pro Ala Pro Pro Arg Gly
            275                 280                 285
Ala Gly Gly Arg Pro Arg Arg Cys Asp Arg Leu Gly Arg Pro Cys Gln
    290                 295                 300
Gly Arg Ala Ala Ser Arg Ala Arg Pro Ala Pro Ala Pro His Pro Ala
305                 310                 315                 320
Asp Leu Ala Asp Phe Val Val Ser Arg Leu Ser
                325                 330
```

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Gly or Glu"

(xi) SEQUENCE DESCRIPTION: SEQ ID NO: 3:

```
Xaa Gly Lys Arg Ile Arg Pro
1               5
```

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "Thr or Met"

(ix) FEATURE:
        (A) NAME/KEY: Modified-site
        (B) LOCATION: 3
        (D) OTHER INFORMATION: /product= "Thr or Ser"

(ix) FEATURE:
        (A) NAME/KEY: Modified-site
        (B) LOCATION: 5
        (D) OTHER INFORMATION: /product= "Val, Ile or Leu"

(xi) SEQUENCE DESCRIPTION: SEQ ID NO: 4:

```
Xaa Ala Xaa Leu Xaa His Asp
1               5
```

(2) INFORMATION FOR SEQ ID NO: 5:

(i) SEQUENCE CHARACTERISTICS:
       (A) LENGTH: 7 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 5:

Ala Ser Leu Leu His Asp Asp
1               5

(2) INFORMATION FOR SEQ ID NO: 6:

(i) SEQUENCE CHARACTERISTICS:
       (A) LENGTH: 6 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 6:

Ala Asp Leu Arg Arg Gly
1               5

(2) INFORMATION FOR SEQ ID NO: 7:

(i) SEQUENCE CHARACTERISTICS:
       (A) LENGTH: 7 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 7:

Leu Ala Gly Asp Phe Leu Leu
1               5

(2) INFORMATION FOR SEQ ID NO: 8:

(i) SEQUENCE CHARACTERISTICS:
       (A) LENGTH: 5 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 8:

Gly Glu Leu Gln Leu
1               5

(2) INFORMATION FOR SEQ ID NO: 9:

(i) SEQUENCE CHARACTERISTICS:
       (A) LENGTH: 6 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 9:

Lys Thr Ala Leu Leu Ile
1               5

(2) INFORMATION FOR SEQ ID NO: 10:

(i) SEQUENCE CHARACTERISTICS:
        (A) LENGTH: 6 amino acids
        (B) TYPE: amino acid
        (C) STRANDEDNESS: <Unk nown>
        (D) TOPOLOGY: linear (ii) MOLECULE TYPE: peptide (xi) SEQUENCE DESCRIPTION: SEQ ID NO: 10:

Phe Gln Leu Ile Asp Asp
1           5

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS: <Unk nown>
        (D) TOPOLOGY: linear (ii) MOLECULE TYPE: peptide (xi) SEQUENCE DESCRIPTION: SEQ ID NO: 11:

Asp Asp Ile Leu Asp Phe
1           5

(2) INFORMATION FOR SEQ ID NO: 12:

(i) SEQUENCE CHARACTERISTICS:
        (A) LENGTH: 7 amino acids
        (B) TYPE: amino acid
        (C) STRANDEDNESS: <Unk nown>
        (D) TOPOLOGY: linear (ii) MOLECULE TYPE: peptide (xi) SEQUENCE DESCRIPTION: SEQ ID NO: 12:

Gly Lys Asn Val Gly Asp Asp
1           5

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: <Unk nown>
        (D) TOPOLOGY: linear (ii) MOLECULE TYPE: peptide (ix) FEATURE:
        (A) NAME/KEY: Modified-si te
        (B) LOCATION: 3
        (D) OTHER INFORMATION: /product= "Leu, Ile or Met"

(ix) FEATURE:
        (A) NAME/KEY: Modified-si te
        (B) LOCATION: 6
        (D) OTHER INFORMATION: /product= "Tyr or Phe"

(ix) FEATURE:
        (A) NAME/KEY: Modified-si te
        (B) LOCATION: 7
        (D) OTHER INFORMATION: /product= "Asn or Thr"

(xi) SEQUENCE DESCRIPTION: SEQ ID NO: 13:

Asp Asp Xaa Leu Asp Xaa Xaa
1           5

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 14:

SRCGGWAARC RBATBCGTCC                                        20

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 15:

AYNGCKWCNC TNBTNCACGA                                        20

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 16:

GGNGGNAARC GNATHCGNCC                                        20

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 17:

GCNTCNCTNC TNCAYGACGA                                        20

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 18:

GCNGAYTTRM GNMGNGG                                                  17

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 19:

YTNGCNGGNG AYTTYTTRTT                                        20

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 20:

KTRWAATCGA GWAHRTCRTC                                        20

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 21:

NARYTGYAAN ARYTCNCC                                          18

(2) INFORMATION FOR SEQ ID NO: 22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 22:

DATNAGNAGN GCNGTYTT                                          18

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 23:

RTCRTCDATY AAYTGRAA                                          18

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 24:

RAARTCNARD ATRTCRTC                                                      18

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 25:

RTCRTCNCCN ACRTTYTTNC C                                                21

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 26:

CCGGCCGACG CAAACCTT                                                       18

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 27:

CTGCTGCACC GCCGGGTC                                                       18

(2) INFORMATION FOR SEQ ID NO: 28:

(i) SEQUENCE CHARACTERISTICS:
        (A) LENGTH: 1219 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 151..1149

(xi) SEQUENCE DESCRIPTION: SEQ ID NO: 28:

```
GATCCCCTCG GCCGCCAGCA GGTCGGCGGC GCGGGTGATG AGAAGCGGGT C GGTGGTGCG         60

CAGAAGCTCT TTCATGACAT GGGAAAGTTA CGCGGCTGTT GCGCATGTGT C CATGGCGT         120

GCAATGGCTG GCGGCGAAAG GGGATCGCTG ATG GGC ATG AAC G AA AAC GTC TCC         174
                                 Met Gly Met Asn Glu Asn Val Ser
                                  1               5

AAG CCG CTC GAC CGG CTC TCC GTG GAA CTG G CC GGG GAT ATG GAC CGG          222
Lys Pro Leu Asp Arg Leu Ser Val Glu Leu A la Gly Asp Met Asp Arg
     10              15                    20

GTC AAT GCG CTG ATC CGC GAG CGC ATG GCC A GC CGC CAC GCC CCC CGC          270
Val Asn Ala Leu Ile Arg Glu Arg Met Ala S er Arg His Ala Pro Arg
 25              30                  35                  40

ATT CCG GAA GTG ACC GCG CAT CTG GTC GAG G CC GGC GGC AAG CGG CTG          318
Ile Pro Glu Val Thr Ala His Leu Val Glu A la Gly Gly Lys Arg Leu
                 45                  50                  55

CGG CCG ATG CTG GTG CTG GCG GCG GCG CGG C TG TGC GGC TAT CAG GGG          366
Arg Pro Met Leu Val Leu Ala Ala Ala Arg L eu Cys Gly Tyr Gln Gly
             60              65                  70

AAC AGC CAT GTG CTG CTG GCC GCG GCG GTC G AG TTC ATC CAT ACC GCG          414
Asn Ser His Val Leu Leu Ala Ala Ala Val G lu Phe Ile His Thr Ala
         75              80                  85

ACG CTT CTG CAC GAC GAC GTG GTC GAT GAA A GC CAG CAG CGG CGC GGC          462
Thr Leu Leu His Asp Asp Val Val Asp Glu S er Gln Gln Arg Arg Gly
         90              95                 100

CGG CCG ACG GCC AAC CTT CTG TGG GAC AAC A AG TCC AGC GTG CTG GTC          510
Arg Pro Thr Ala Asn Leu Leu Trp Asp Asn L ys Ser Ser Val Leu Val
105             110                 115                 120

GGC GAC TAC CTG TTC GCG CGC AGC TTC CAG C TG ATG GCG GAT ACG GAA          558
Gly Asp Tyr Leu Phe Ala Arg Ser Phe Gln L eu Met Ala Asp Thr Glu
             125                 130                 135

AGC ATG CAG GTC ATG CGC ATC TTG GCC AAT G CC AGC GCC ACC ATC GCC          606
Ser Met Gln Val Met Arg Ile Leu Ala Asn A la Ser Ala Thr Ile Ala
             140                 145                 150

GAG GGC GAG GTG CTG CAG CTG ACC GCC GCG C AG GAC GTC TCG ACC ACC          654
Glu Gly Glu Val Leu Gln Leu Thr Ala Ala G ln Asp Val Ser Thr Thr
         155                 160                 165

GAG GAC ACC TAT ATC CAG ATC GTG CGC GGC A AG ACA GCG GCG CTG TTT          702
Glu Asp Thr Tyr Ile Gln Ile Val Arg Gly L ys Thr Ala Ala Leu Phe
170             175                 180

TCC GCC GCG ACC GAG GCG GGG GCG GTG GTG G CC GGC GCC GAC CCG GCG          750
Ser Ala Ala Thr Glu Ala Gly Ala Val Val A la Gly Ala Asp Pro Ala
185             190                 195                 200

GTG CAG CAG GCG CTG TTC GAC TAT GGC GAT G CG CTG GGG ATC GCC TTC          798
Val Gln Gln Ala Leu Phe Asp Tyr Gly Asp A la Leu Gly Ile Ala Phe
             205                 210                 215

CAG ATC GTG GAC GAC CTG CTG GAT TAC GGC G GC TCG ACC ACG ACC ATC          846
Gln Ile Val Asp Asp Leu Leu Asp Tyr Gly G ly Ser Thr Thr Thr Ile
             220                 225                 230

GGC AAG AAC GTC GGC GAC GAT TTC CGC GAG C GC AAG CTG ACG CTG CCG          894
Gly Lys Asn Val Gly Asp Asp Phe Arg Glu A rg Lys Leu Thr Leu Pro
         235                 240                 245

GTG ATC AAG GCC ATC GCC CGC GCC GAC GAG G CC GAG CGC GCC TTC TGG          942
Val Ile Lys Ala Ile Ala Arg Ala Asp Glu A la Glu Arg Ala Phe Trp
         250                 255                 260

GAA CGC ACC ATC GGC CAG GGC CGG CAG GAC G AG GCC GAC CTG GCC ACC          990
Glu Arg Thr Ile Gly Gln Gly Arg Gln Asp G lu Ala Asp Leu Ala Thr
265             270                 275                 280
```

```
GCG CTG GAG ATC CTG CGC CGC CGC GAG GCG C TG GAG GCC GCC CGC GCC     1038
Ala Leu Glu Ile Leu Arg Arg Arg Glu Ala L eu Glu Ala Ala Arg Ala
                285                 290                 295

GAT GCG ATC GCC TGG GCC GGC CGT GCC AAG G CC GCG CTG CAA GCC GCG     1086
Asp Ala Ile Ala Trp Ala Gly Arg Ala Lys A la Ala Leu Gln Ala Ala
                300                 305                 310

CCC GAC CAG CCC CTG CGC CGC ATC CTG GCG G AC CTG GCG GAT TTC GTG     1134
Pro Asp Gln Pro Leu Arg Arg Ile Leu Ala A sp Leu Ala Asp Phe Val
                315                 320                 325

GTC TCG CGC CTG TCC TGACCAAAGC CCCCGCACAA ATGAAAAA GC CCGGCGCATG     1189
Val Ser Arg Leu Ser
            330

TGCCGGGCTT TTCCTTTGCC TGAAGCGCTG                                    1219

(2) INFORMATION FOR SEQ ID NO: 29:

(i) SEQUENCE CHARACTERISTICS:
        (A) LENGTH: 333 amino acids
        (B) TYPE: amino acid
        (D) TOPOLOGY: linear (ii) MOLECULE TYPE: protein (xi) SEQUENCE DESCRIPTION: SEQ ID NO: 29:

Met Gly Met Asn Glu Asn Val Ser Lys Pro L eu Asp Arg Leu Ser Val
 1               5                  10                  15

Glu Leu Ala Gly Asp Met Asp Arg Val Asn A la Leu Ile Arg Glu Arg
                20                  25                  30

Met Ala Ser Arg His Ala Pro Arg Ile Pro G lu Val Thr Ala His Leu
            35                  40                  45

Val Glu Ala Gly Gly Lys Arg Leu Arg Pro M et Leu Val Leu Ala Ala
        50                  55                  60

Ala Arg Leu Cys Gly Tyr Gln Gly Asn Ser H is Val Leu Leu Ala Ala
 65                 70                  75                  80

Ala Val Glu Phe Ile His Thr Ala Thr Leu L eu His Asp Asp Val Val
                85                  90                  95

Asp Glu Ser Gln Gln Arg Arg Gly Arg Pro T hr Ala Asn Leu Leu Trp
                100                 105                 110

Asp Asn Lys Ser Ser Val Leu Val Gly Asp T yr Leu Phe Ala Arg Ser
            115                 120                 125

Phe Gln Leu Met Ala Asp Thr Glu Ser Met G ln Val Met Arg Ile Leu
130                 135                 140

Ala Asn Ala Ser Ala Thr Ile Ala Glu Gly G lu Val Leu Gln Leu Thr
145                 150                 155                 160

Ala Ala Gln Asp Val Ser Thr Thr Glu Asp T hr Tyr Ile Gln Ile Val
                165                 170                 175

Arg Gly Lys Thr Ala Ala Leu Phe Ser Ala A la Thr Glu Ala Gly Ala
                180                 185                 190

Val Val Ala Gly Ala Asp Pro Ala Val Gln G ln Ala Leu Phe Asp Tyr
            195                 200                 205

Gly Asp Ala Leu Gly Ile Ala Phe Gln Ile V al Asp Asp Leu Leu Asp
        210                 215                 220

Tyr Gly Gly Ser Thr Thr Thr Ile Gly Lys A sn Val Gly Asp Asp Phe
225                 230                 235                 240

Arg Glu Arg Lys Leu Thr Leu Pro Val Ile L ys Ala Ile Ala Arg Ala
                245                 250                 255

Asp Glu Ala Glu Arg Ala Phe Trp Glu Arg T hr Ile Gly Gln Gly Arg
```

-continued

```
                    260                  265                  270
Gln Asp Glu Ala Asp Leu Ala Thr Ala Leu G lu Ile Leu Arg Arg Arg
                275                  280                  285
Glu Ala Leu Glu Ala Ala Arg Ala Asp Ala I le Ala Trp Ala Gly Arg
    290                  295                  300
Ala Lys Ala Ala Leu Gln Ala Ala Pro Asp G ln Pro Leu Arg Arg Ile
305                  310                  315                  320
Leu Ala Asp Leu Ala Asp Phe Val Val Ser A rg Leu Ser
                325                  330
```

(2) INFORMATION FOR SEQ ID NO: 30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 30:

ATCGCCCATG GGCATGAACG AAAACGTCTC                                                30

(2) INFORMATION FOR SEQ ID NO: 31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO: 31:

GAGGGATCCT ATAACAACTG AGGCAGCG                                                  28

DECAPRENYL DIPHOSPHATE SYNTHETASE GENE

This is a division of U.S. patent application Ser. No. 09/025,819, filed Feb. 19, 1998, now U.S. Pat. No. 6,225,097, which is incorporated herein by reference in its entirety.

BACKGROUND OF THE INVENTION

1. Field of the Invention

The present invention relates to a decaprenyl diphosphate synthetase, a gene coding for the synthetase, a recombinant vector comprising the gene, a transformant transformed with the vector, a method for producing a decaprenyl diphosphate synthetase, and a method for producing ubiquinone-10.

2. Description of the Prior Art

Isoprenoids are the most varied group of compounds including more than 23,000 species occurring in nature. They include sterols, carotenoids, sugar carrier lipids, prenyl quinones, prenylated proteins, etc. (FIG. 1). Those enzymes which catalyze the formation of carbon skeletons that will be the basis for the biosynthesis of these isoprenoid compounds (i.e., enzymes which catalyze the head-to-tail type condensation polymerization of isopentenyl diphosphate (IPP) that is 5-carbon isoprene unit) are generically called as prenyl diphosphate synthetase. Prenyl diphosphate synthetase is classified into 4 groups depeding on the chain length, conformation, etc. of the prenyl diphosphate generated (Table 1).

TABLE 1

Classification of Prenyltransferase

| Group | Structure | Major Characteristic | Products |
|---|---|---|---|
| Short-chain prenyl diphosphate synthetase | Homodimer | Soluble | $C_{16}$, $C_{20}$ |
| Medium-chain prenyl diphosphate synthetase | Heterodimer | Soluble | $C_{30}$, $C_{35}$ |
| (E)-polyprenyl diphosphate synthetase | Homodimer | Activated by carrier proteins. | $C_{40}$, $C_{45}$, $C_{50}$ |
| (Z)-polyprenyl diphosphate synthetase | Homodimer | Activated by lipids. | $C_{45}$, $C_{55}$ |

Short-chain prenyl diphosphate synthetase (prenyltransferase I) includes geranyl diphosphate (GPP, C10) synthetase, farnesyl diphosphate (FPP, C15) synthetase (Eberhardt, N. L. et al., (1975) J. Biol. Chem. 250:863–866), geranylgeranyl diphosphate (GGPP, C20). synthetase (Sagami, H. et al. (1994) J. Biol. Chem. 269:20561–20566) and the like. The short-chain prenyl diphosphates biosynthesized by these enzymes are water-soluble. They may be supplied as an allyl primer substrate for polyprenyl diphosphate synthetase belonging to other groups.

Medium-chain prenyl diphosphate synthetase (prenyltransferase II) includes hexaprenyl diphosphate (HexPP, C30) synthetase (Fujii, H. et al., (1982) J. Biol. Chem., 257:14610), heptaprenyl diphosphate (HepPP, C35) synthetase (Takahashi, I. et al., (1980) J. Biol Chem., 255: 4539) and the like. These enzymes are greatly different from the short-chain prenyl diphosphate synthetase described above in that they are heterodimeric enzymes composed of two proteins each of which does not have a catalytic function alone. Usually, these two proteins are dissociated, but when a substrate is present, they associate with each other to manifest a function as an enzyme. Although those products produced by such enzymes are highly hydrophobic and apt to form micelles, they do not require lipids nor surfactants for the manifestation of their enzyme activity. This is considered due to the fact that the medium-chain prenyl diphosphate synthetase is a special system in which such dynamic dissociation and association are repeated.

E-type long-chain prenyl diphosphate synthetase (prenyltransferase III) includes octaprenyl diphosphate (OctPP, C40) synthetase, decaprenyl diphosphate (DPP, C50) synthetase and the like. Unlike prenyltransferase II, these enzymes are undissociable homodimers and activated by polyprenyl diphosphate carrier proteins (Ohnuma, S. et al., (1991) J. Biol. Chem. 266:23706–23713). This activation is believed to maintain the catalyst turnover by removing hydrophobic reaction products from the active sites of these enzymes.

Z-type long-chain prenyl diphosphate synthetase (prenyltransferase IV) includes nonaprenyl diphosphate (E,E-farnesyl-all-Z-hexaprenyl diphosphate, C45) synthetase, undecaprenyl diphosphate (E,E-farnesyl-all-Z-octaprenyl diphosphate, C55) synthetase and the like. Reaction products generated by these enzymes work as sugar carrier lipids in the biosynthesis of bacterial cell walls. These enzymes need the addition of a phospholipid or surfactant for the manifestation of their activity. DPP synthetase, which is classified into prenyltransferase III, is also known to require a surfactant for the manifestation of its enzyme activity.

A soil bacterium *Paracoccus denitrificans* is a bacterium which is believed to be the origin of human mitochondria. The respiratory chain and the oxidative phosphorylation mechanism of this bacterium are more efficient and more united as one organization than those of other bacteria. Thus, the characteristics of *P. denitrificans* are more closer to those of mitochondria (John, P. et al., (1975) Nature, 254, 495–498). Three types of prenyl diphosphate synthetase activities have been confirmed from *P. denitrificans* (FIG. 2). They are activities of (i) FPP synthetase which catalyzes E-type condensation of dimethylallyl diphosphate (DMAPP) with 2 molecules of IPP to produce FPP; (ii) nonaprenyl diphosphate (NPP) synthetase which catalyzes Z-type condensation of FPP with 6 molecules of IPP to produce NPP (Ishii, K. et al., (1986) Biochem. J., 233, 773–777); and (iii) DPP synthetase which catalyzes E-type condensation of FPP with 7 molecules of IPP to produce DPP (Ishii K. et al., (1983) Biochem. Biophys. Res. Commun., 116, 500–506).

NPP produced by NPP synthetase becomes a sugar carrier lipid which is essential for the biosynthesis of the cell wall of this bacterium. However, unlike several E-type prenyl diphosphate synthetases which have been already cloned and analyzed, prenyl diphosphate synthetases such as NPP synthetase and undecaprenyl diphosphate synthetase which catalyze Z-type condensation reaction have not been elucidated yet in relationships between their structures and enzymatic functions.

DPP produced by DPP synthetase is metabolized on the prenyl side chain of ubiquinone-10 (a constituent of the electron transport system) produced by this bacterium. All of the C30–C50 polyprenyl diphosphates biosynthesized by bacterial prenyltransferase II or III are provided as a side chain precursor of the corresponding menaquinone or ubiquinone. Therefore, the chain length of the product of each enzyme is directly reflected in the side chain length of the prenylquinone of the bacterium from which the enzyme is derived. Among prenylquinones, ubiquinone-10 is industrially extracted from *Paracoccus denitrificans* and used as pharmaceuticals since it has the same side chain length as that of human coenzyme Q (CoQ). Ubiquinone has been known to be effective for chronic heart diseases (Yamamura, T. (1977) Clinical Status of Coenzyme Q and Prospects 281–298). Ubiquinone-10 is also effective as an antiarrhythmic agent and, thus, is utilized for the prevention of arrhythmia and the like (Fujioka, T. et al. (1983) Tohoku J. Exp. Med. 141, 453–463).

SUMMARY OF THE INVENTION

It is the object of the present invention to provide a decaprenyl diphosphate synthetase, a gene coding for the synthetase, a recombinant vector comprising the gene, a transformant transformed with the vector, a method for producing the decaprenyl diphosphate synthetase, and a method for producing ubiquinone-10.

As a result of intensive and extensive researches toward the solution of the above assignment, the present inventor has succeeded in cloning a gene coding for a long-chain decaprenyl diphosphate synthetase from *Paracoccus denitrificans*. Thus, the present invention has been achieved.

The present invention relates to a recombinant protein (a) or (b) described below:

(a) a protein having the amino acid sequence shown in SEQ ID NO:2

(b) a protein which has the amino acid sequence shown in SEQ ID NO:2 having deletion, substitution or addition of at least one amino acid and which has decaprenyl diphosphate synthetase activity.

The present invention also relates to a gene coding for the recombinant protein (a) or (b) described above. Specific examples of this gene include a gene comprising the base sequence shown in SEQ ID NO: 1.

Further, the present invention relates to a recombinant vector comprising the above gene.

The present invention further relates to a transformant transformed with the above vector.

The present invention further relates to a method for producing a decaprenyl diphosphate synthetase comprising culturing the above transformant in a medium and recovering a decaprenyl diphosphate synthetase from the resultant culture.

The present invention further relates to a method for producing ubiquinone-10comprising extracting ubiquinone-10 from the above transformant.

BRIEF DESCRIPTION OF THE DRAWINGS

FIG. 3 is a diagram showing the design of PCR primers.

FIG. 4 is a photograph showing the results of PCR.

FIG. 5 is a diagram showing comparison of amino acid homology.

FIGS. 7A and 7B provide two electrophorograms showing the results of Southern hybridization.

FIG. 11 is a diagram showing the open reading frame contained in plasmid p11A1.

FIG. 12 is a diagram showing comparison of amino acid sequences for various prenyltransferases.

DETAILED DESCRIPTION OF THE INVENTION

Figure 1:
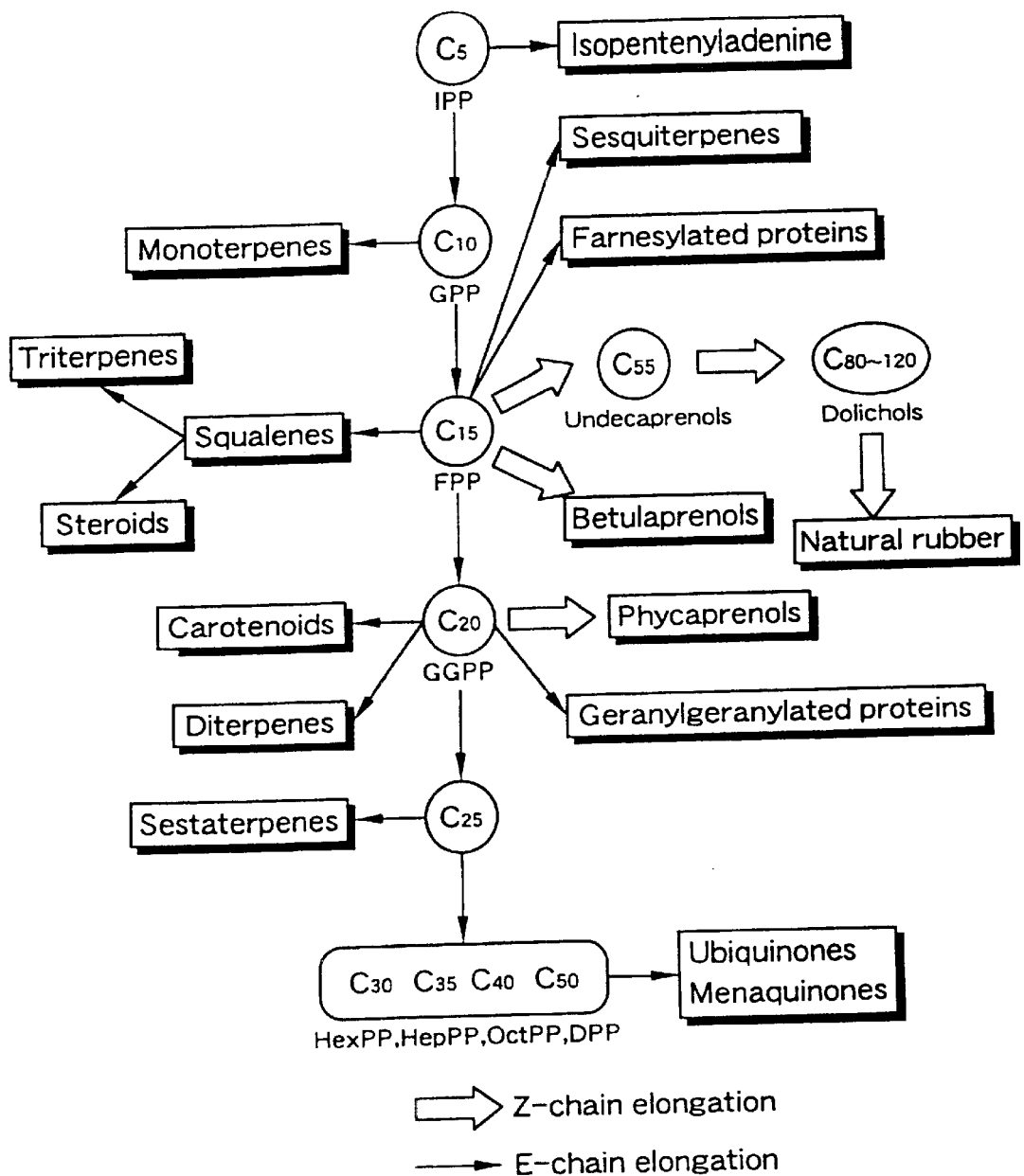
FIG. 1 is a diagram showing the biosynthesis of isoprenoid compounds.
Figure 2:
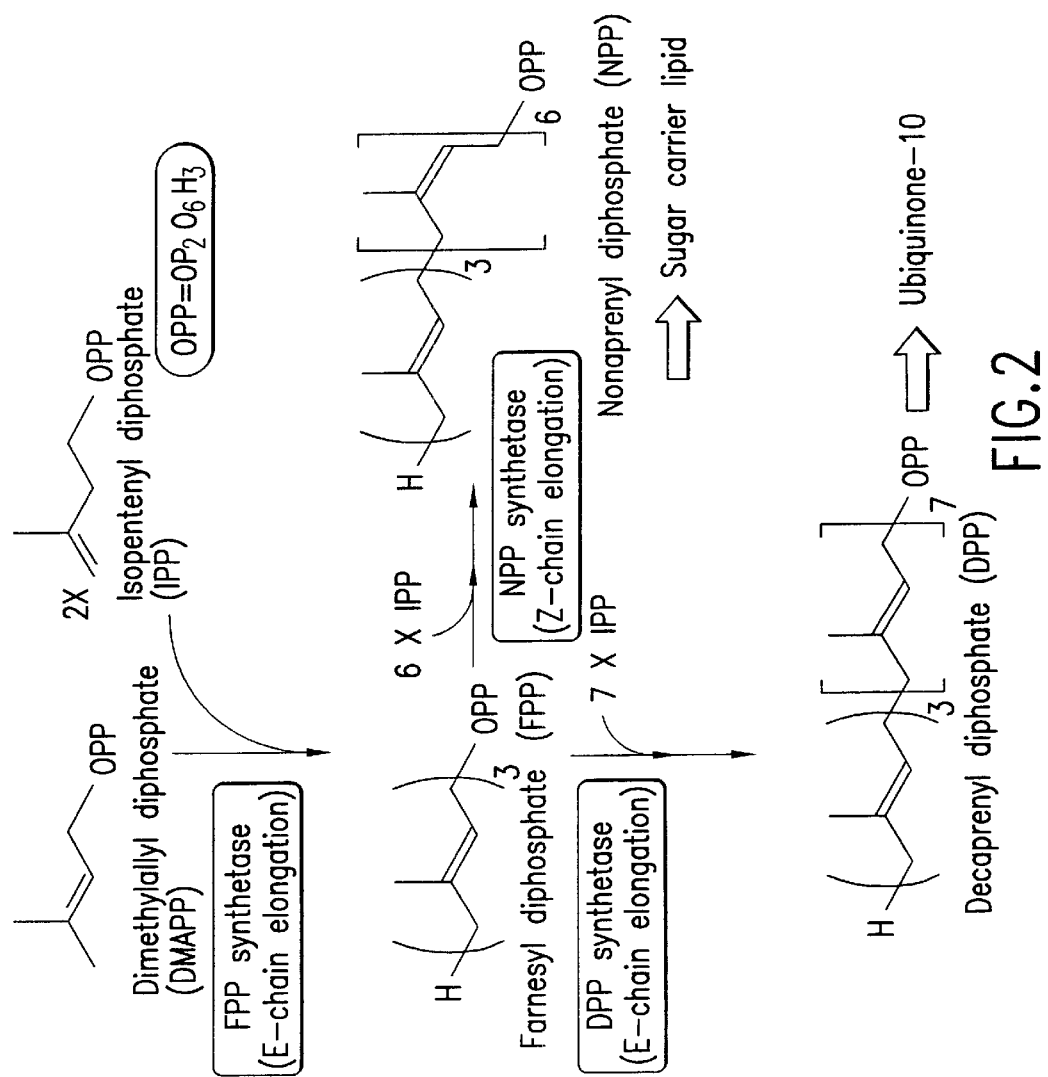
FIG. 2 is a diagram showing the biosynthetic pathway of prenyl diphosphates in *P. denitrificans*.

Hereinbelow, the present invention will be described in detail.

It is known that prenyl diphosphate synthetases (hereinafter, sometimes referred to as "prenyltransferase(s)") have 7 regions which have been preserved highly beyond species (Koyama, T. et al., (1993) J. Biochem. 113:355). In the present invention, degenerate oligonucleotides for use as primers are designed based on the amino acid sequences highly preserved among various prenyltransferases. Using these primers in various combinations, PCR is performed with genomic DNA from the soil bacterium *Paracoccus denitrificans* (hereinafter referred to as "=*P. denitrificans*") as a template. The gene of the present invention can be obtained by screening the genomic DNA using one of the amplified partial sequences as a probe.

1. Cloning of a Gene Coding for a Prenyl Diphosphate Synthetase (1) Preparation of Genomic DNA First, genomic DNA is prepared from cultures cells of a prenyl diphosphate synthetase producing bacterium such as the soil bacterium *P. denitrificans*.

The preparation of genomic DNA may be performed by any of the conventional methods. For example, genomic DNA can be prepared easily by the following procedures. The above bacterium is inoculated into a medium containing 2 g of yeast extract, 10 g of Polypeptone, 1 g of $MgSO_4 \cdot 7H_2O$ and 1 liter of distilled water (802 medium) and cultured at 30° C. for one to several days (until saturation); subsequently, bacterial cells are treated with lysozyme and further treated with a surfactant such as sodium lauryl sulfate; thereafter, proteins are removed therefrom with an organic solvent such as phenol, chloroform or ether; then, genomic DNA is precipitated with ethanol.

Subsequently, a genomic DNA library is prepared by ligating the resultant genomic DNA to a vector plasmid. This preparation may be performed by conventional methods. For example, genomic DNA strand and plasmid DNA strand are cut with an appropriate restriction enzyme (e.g., EcoRI, BamHI, Hind III, Sau3AI, MboI, PstI); then, these strands are just treated with a DNA ligase (e.g., T4 DNA ligase), or they are treated with a DNA ligase after treatment with a terminal transferase or DNA polymerase depending on the states of the resultant fragment ends, to thereby ligate DNA strands (Molecular Cloning, Cold Spring Harbor Laboratory, 269, 1982; Nelson, T. et al. Methods in Enzymol., 68, 41, 1979). As a vector useful for this purpose, λ phage vectors (e.g., λgt10, Charon 4A, EMBL-3), plasmid vectors (e.g., pBR322, pSC101, pUC19, pUC119, pACYC117) or like may be enumerated. After incorporation of the above DNA fragment into such a vector, *Escherichia coli*(e.g., DH1, HB101, JM109, C600, MV1184, TH2) is transformed with the vector to obtain a genomic DNA library.

(2) Preparation of Probes for Screening

First, probes to be used for screening the above genomic DNA library by hybridization are prepared. For the preparation of probes which are highly specific to a DNA of interest, it is considered appropriate to prepare oligonucleotides coding for the regions with highly preserved amino acid residues among various organism species. These probes can be obtained by conventional chemical synthesis. As amino acid sequences which satisfy the above conditions, the following preserved amino acid sequences are selected based on FIG. 3.

The sequence "(Gly or Glu) Gly Lys Arg Ile Arg Pro" (SEQ ID NO: 1) in Region I

The sequences "(Thr or Met) Ala (Ser or Thr) Leu (Val, Ile or Leu) His Asp" (SEQ ID NO: 4), "Ala Ser Leu Leu His Asp Asp" (SEQ ID NO: 5) and "Ala Asp Leu Arg Arg Gly" (SEQ ID NO: 6) in Region II The sequence "Leu Ala Gly Asp Phe Leu Leu" (SEQ ID NO: 7) in Region III The sequence "Gly Glu Leu Gln Leu" (SEQ ID NO: 8) in Region IV The sequence "Lys Thr Ala Leu Leu Ile" (SEQ ID NO: 9) in Region V The sequences "Phe Gln Leu Ile Asp Asp" (SEQ ID NO: 10), "Asp Asp Ile Leu Asp Phe" (SEQ ID NO: 11), "Gly Lys Asn Val Gly Asp Asp" (SEQ ID NO: 12) and "Asp Asp (Leu, Ile or Met) Leu Asp (Tyr or Phe) (Asn or Thr)" (SEQ ID NO: 13) in Region VI.

Regions, I, II, III, IV, V and VI correspond to amino acid positions from 43 to 53, from 74 to 95, from 110 to 119, from 145 to 150, from 170 to 175 and from 204 to 230, respectively, of the amino acid sequence for a *Bacillus stearothermophylus*-derived heptaprenyl diphosphate synthetase disclosed in Koike- Takeshita, A. et al., (1995) J. Biol. Chem. 270:18396–18400.

Examination of preserved amino acid sequences in various organism species can be performed among known prenyl diphosphate synthetases, such as FPS synthetases from *Bacillus stearothermophylus, Escherichia coli, Saccharomyces cerevisiae*, rat and human; GGPS synthetases from *Erwinia herbicola* and *Erwinia uredovora*; and HexPS synthetase from *Saccharomyces cerevisiae*.

Based on the amino acid sequences thus selected, the oligonucleotide probes shown below are prepared.

Briefly, in the present invention, the following 12 degenerate primers are designed based on highy preserved amino acid sequences among various prenyltransferases and on those sequences which are peculiar to medium- or long-chain prenyltransferases such as hexaprenyl diphosphate (HexPP, C30) synthetase, heptaprenyl diphosphate (Hepp, C35) (Koike-Takeshita, A. et al. (1995) J. Biol. Chem. 270:18396–18400) synthetase and octaprenyl diphosphate (OctPP, C40) (Okada, K., J. Bacteriol. 179, 3058–3060 (1997) synthetase.

Sense primers:

S1 (designed based on SEQ ID NO: 3):
5'-(CG) (AG)CGG(AT)AA(AG)C(AG) (CGT)AT(CGT) CGTCC-3'(SEQ ID NO: 14)

S2 (designed based on SEQ ID NO: 4):
5'-A(CT)(ACGT)GC(GT)(AT)C(ACGT)CT(ACGT)(CGT) T(ACGT)CACGA-3' (SEQ ID NO: 15)

S3 (designed based on SEQ ID NO: 3):

5'-GG(ACGT)GG(ACGT)AA(AG)CG(ACGT)AT(ACT) CG(ACGT)CC-3' (SEQ ID NO: 16)

S4 (designed based on SEQ ID NO: 5):
5'-GC(ACGT)TC(ACGT)CT(ACGT)CT(ACGT)CA(CT) GACGA-3' (SEQ ID NO: 17)

S5 (designed based on SEQ ID NO: 6):
5'-GC(ACGT)GA(CT)TT(AG)(AC)G(ACGT)(AC)G (ACGT)GG-3' (SEQ ID NO: 18)

S6 (designed based on SEQ ID NO: 7):
5'-(CT)T(ACGT)GC(ACGT)GG(ACGT)GA(CT)TT(CT) TT(AG)TT-3' (SEQ ID NO: 19)

Antisense primers:

A1 (designed based on SEQ ID NO: 13):
5'-(GT)T(AG)(AT)AATCGAG(TA)A(ACT)(AG)TC(AG) TC-3' (SEQ ID NO: 20)

A2 (designed based on SEQ ID NO: 8):
5'-(ACGT)A(AG)(CT)TG(CT)AA(ACGT)A(AG)(CT)TC (ACGT)CC-3' (SEQ ID NO: 21)

A3 (designed based on SEQ ID NO: 9):
5'-(AGT)AT(ACGT)AG(ACGT)AG(ACGT)GC(ACGT) GT(TC)TT-3' (SEQ ID NO: 22)

A4 (designed based on SEQ ID NO: 10):
5'-(AG)TC(AG)TC(AGT)AT(CT)AA(CT)TG(AG)AA-3' (SEQ ID NO: 23)

A5 (designed based on SEQ ID NO: 11):
5'-(AG)AA(AG)TC(ACGT)A(AG)(AGT)AT(AG)TC(AG) TC-3' (SEQ ID NO: 24)

A6 (designed based on SEQ ID NO: 12):
5'-(AG)TC(AG)TC(ACGT)CC(ACGT)AC(AG)TT(CT)TT (ACGT)CC-3' (SEQ ID NO: 25)

(3) Cloning of a Part of a Prenyl Diphosphate Synthetase Gene

The screening of *P. denitrificans* genomic DNA for the gene of the present invention can be performed by conventional methods such as Southern hybridization, colony hybridization, PCR or a combination of these methods.

For example, genomic DNA from *P. denitrificans* is subjected to PCR using a combination of the primers described above to thereby amplify a DNA fragment containing a part of a prenyl diphosphate synthetase gene. The fragment which is believed to contain a part of the target gene is separated by electrophoresis and recovered. After ligation of the DNA fragment to a vector, *E. coli* is transformed with the vector, and the DNA fragment is cloned. The thus obtained DNA fragment (pCR14) is suitable as a probe for obtaining a full length prenyl diphosphate synthetase gene.

(4) Cloning of a Full Length Prenyl Diphosphate Synthetase Gene

As described above, probe pCR14 is a DNA fragment containing a part of the prenyl diphosphate synthetase gene of *P. denitrificans*. Thus, the screening for a gene encoding the peptide of the prenyl diphosphate synthetase of the invention is performed, for example, as described below using pCR14.

The genomic DNA partially digested with Sau3AI is electrophoresed. Resultant DNA fragments of 5–10 kbp are extracted from the agarose gel and inserted into the BamHI site of pUC119. With this plasmid, *E. coli* JM109 is transformed to prepare a DNA library. Then, colony hybridization is performed with pCR14 as a probe.

(5) Determination of the Base Sequence

Each of the clones thus obtained is digested with an appropriate restriction enzyme, followed by agarose gel electrophoresis. From the migration pattern and distance, a restriction map is prepared. Based on this map, deletion of the DNA fragment (i.e., to make the DNA fragment shorter) is carried out to thereby obtain a minimum clone exhibiting activity. Then, the base sequence for the activity-exhibiting DNA is analyzed.

The base sequence may be determined using two plasmids which contain the same insert DNA truncated at one end in opposite directions.

The screened clone is digested with an appropriate restriction enzyme (such as EcoRI, PstI) and cloned into a plasmid (such as pUC119, pUC19). Then, the base sequence for the DNA of interest can be determined by conventional base sequence analysis methods, for example, the dideoxy method by Sanger et al. (Sanger, F. et al., Proc. Natl. Acad. Sci. USA (1977) 74:5463). The determination of the base sequence may be performed with an automatic base sequence analyzer such as T7 Sequencing Kit (Pharmacia).

(6) Identification of the Gene

A region which is expected to be a prenyl diphosphate synthetase gene is integrated into an expression vector, with which E. coli is transformed. The transformant is cultured and resultant cells are crushed to obtain a crude enzyme extract. By determining the activity of this extract, the prenyl diphosphate synthetase, particularly, decaprenyl diphosphate synthetase of the invention can be identified. Also, by determining the length of the ubiquinone side chain of the transformant, the gene can be identified.

The base sequence for the gene coding for the prenyltransferase of the invention is shown in SEQ ID NO: 1. The amino acid sequence for the prenyltransferase of the invention is shown in SEQ ID NO: 2. However, the amino acid sequence of SEQ ID NO: 2 may have a mutation such as deletion, substitution or addition of at least one amino acid (preferably, one or several amino acids) as long as it can exhibit prenyltransferase activity. In addition to the base sequence shown in SEQ ID NO: 1, a base sequence which codes for the same polypeptide and which is only different from SEQ ID NO: 1in a degenerate codon(s) is also. included in the gene of the present invention.

Introduction of the above mutation can be performed easily by conventional methods such as the method of Kunkel (Kunkel, T. A., Proc. Natl. Acad. Sci. (1985) 82:488).

Once the base sequence has been thus determined, the target gene can be obtained by hybridization with a DNA fragment prepared by chemical synthesis or PCR.

2. Preparation of a Recombinant Vector and a Transformant

A recombinant vector of the invention can be obtained by integrating the gene of the invention into an appropriate vector. A transformant of the invention can be obtained by introducing the recombinant vector into a host which is compatible with the initial vector.

A purified gene is inserted into a restriction site or multi-cloning site of a suitable vector DNA to obtain a recombinant vector. With this vector, a host is transformed.

A vector DNA into which a DNA fragment is inserted is not particularly limited as long as it is replicable in a host cell. For example, a plasmid DNA or phage DNA may be used. As a plasmid DNA, plasmid pUC118 (Takara Shuzo), plasmid pUC119 (Takara Shuzo), pBluescript SK+ (Stratagene), pGEM-T (Promega) or the like may be enumerated. As a phage DNA, M13mp18, M13mp19 or the like may be enumerated.

As a host, any host may be used as long as it can express the gene of interest. Either an eukaryotic or prokaryotic cell may be used. For example, bacteria such as *Escherichia coli*, *Bacillus subtilis*; yeast such as *Saccharomyces cerevisiae*; and animal cells such as COS cells, CHO cells, etc. may be enumerated.

When a bacterium such as *E. coli* is used as a host, preferably the recombinant vector of the invention is capable of autonomous replication in the host and yet has a constitution comprising a promoter, the gene of the invention and a transcription terminator sequence. Specific examples of such *E. coli* include XL1-Blue (Stratagene) and JM109 (Takara Shuzo). Specific examples of an expression vector include pTrc99A and pET expression systems. As a promoter, any promoter may be used as long as it can express the gene of interest in the host such as *E. coli*. Specific examples of the promoter include *E. coli*- or phage-derived promoters such as trp promoter, lac promoter, PL promoter and PR promoter. In the present invention, the transformation of *E. coli* can be performed, for example, by the method of Hanahan (Hanahan, D., J. Mol. Biol. (1983) 166:557).

When yeast is used as a host, an expression vector such as YEp13 or YCp50 may be used. As a promoter, gal 1 promoter or gal 10 promoter may be used, for example. As a method for introducing a recombinant vector into yeast, electroporation (Becker, D. M. Methods. Enzymol. (1991) 194:182–187), the spheroplast method (Hinnen, A., Proc. Natl. Acad. Sci. USA (1978) 75:1929–1933), the lithium acetate method (Ito, H., J. Bacteriol. (1983) 153:163–168) or the like may be enumerated.

When an animal cell is used as a host, an expression vector such as pSG5, pREP4 or pZeoSV may be used. As a method for introducing a recombinant DNA into an animal cell, electroporation, the calcium phosphate precipitation method, or the like may be enumerated.

When a plasmid DNA is used as a vector DNA, if an EcoRI DNA fragment is to be inserted thereinto for example, the plasmid DNA is predigested with the restriction enzyme EcoRI before the insertion. Then, the DNA fragment and the digested vector DNA are mixed. The resultant mixture is treated with, for example, T4 DNA ligase (Takara Shuzo) to obtain a recombinant vector.

3. Production of the Prenyltransferase

The prenyltransferase of the invention can be produced by culturing a transformant carrying the recombinant vector obtained above. The culture method may be the conventional solid culture, but preferably the liquid culture is employed.

As a medium for culturing the transformant, a medium containing at least one nitrogen source selected from yeast extract, Peptone and meat extract; at least one inorganic salt such as dipotassium hydrogenphosphate, magnesium sulfate or ferric chloride; and, if necessary, sugar materials, antibiotics and vitamins may be used, for example. If necessary, IPTG or the like may be added to the medium to induce the expression of the gene. The pH of the medium at the start of culture is adjusted to 6.8–7.5. The culture is conducted usually at 28–42° C., preferably at around 37° C., for 5 hours to overnight. Aeration agitation culture, shaking culture, or the like may be employed.

After completion of the culture, the prenyltransferase of the invention may be recovered by conventional protein purification techniques.

Briefly, cells are crushed by lysis treatment with an enzyme such as lysozyme, sonication, grinding treatment or the like to release the prenyltransferase outside the cells.

Then, insoluble materials are removed by filtration, centrifugation or the like to thereby obtain a crude polypeptide solution.

For further purification of the peptide from the above crude polypeptide solution, conventional protein purification methods may be used. For example, ammonium sulfate fractionation, ion exchange chromatography, hydrophobic chromatography, gel filtration chromatography, affinity chromatography and electrophoresis may be used independently or in combination.

4. Production of Ubiquinone-10

Ubiquinones are known as a constituent of the electron transport system in a number of organisms. The length of their isoprenoid side chains varies with organism species. *E.coli* ubiquinone has an isoprenoid side chain of 8 isoprene units supplied by oPP synthetase; the ubiquinone of budding yeast *Saccharomyces cerevisiae* has a side chain of 6 isoprene units; and human ubiquinone has a side chain of 10 isoprene units.

Generally, *E.coli* ubiquinone does not have an isoprenoid side chain of 10 isoprene units. However, a ubiquinone with an isoprenoid side chain of 10 isoprene units (ubiquinone-10) can be obtained from a transformant *E.coli* into which the gene of the invention has been introduced. By crushing the transformant *E.coli* by sonication or the like, extracting the cell components with hexane and finally applying them to HPLC, ubiquinone-10 can be obtained.

PREFERRED EMBODIMENTS OF THE INVENTION

Hereinbelow, the present invention will be described in more detail with reference to the following Examples, which should not be construed as limiting the technical scope of the invention.

EXAMPLE 1

Cloning of a Prenyltransferase Gene

It is known that prenyltransferases have 7 regions which have been highly preserved beyond species. Then, the present inventor designed degenerate oligonucleotides based on those highly preserved amino acid sequences among various transferases. Using these oligonucleotides as primers in various combinations, PCR was performed with genomic DNA from *P. denitrificans* as a template. Using the amplified partial sequence as a probe, screening was conducted to clone a prenyltransferase gene.

The restriction enzymes and other DNA modification enzymes used in the cloning were obtained from Takara Shuzo, Toyobo and New England BioLabs.

(1) Preparation of Genomic DNA from *P. denitrificans* and Creation of a Genomic Library

*P. denitrificans* was inoculated into 100 ml of 802 medium (10 g of Polypeptone, 2 g of yeast extract, 1 g of $MgSO_4 \cdot 7H_2O$, 1 liter of distilled water, pH 7.0) and cultured at 30° C. until saturation. Then, cells were harvested, and genomic DNA was prepared according to the method of Saito et al. (Biochim. Biophys. Acta 72, 619–629 (1963))

*P. denitrificans* was obtained from American Type Culture Collection (ATCC14907).

The genomic DNA from *P. denitrificans* was partially digested with a restriction enzyme. DNA fragments of a specific length were recovered. Then, a library was prepared. By these procedures, screening efficiency is improved compared to the screening of an entire genomic library.

Briefly, 1 U of Sau3A1 was added to 50 μg of the genomic DNA. The resultant mixture was incubated at 37° C. A specific amount of sample was taken in every 5 minutes from the start of the incubation up to 90 minutes. Then, the reaction was terminated. Each sample was electrophoresed on 0.8% agarose gel. Fragments of 5–10 kbp were recovered from the gel and ligated to pUC119-BamHI vector individually. With this vector, *E. coli* DH5α was transformed. The resultant transformants were cultured in LB medium to prepare glycerol stocks having a glycerol concentration of 30%. Thus, 10 libraries each containing about 2000 clones were prepared. From these libraries, plasmid DNAs were recovered.

(2) Design of PCR Primers

In the present invention, the following 12 degenerate primers were designed based on highly preserved amino acid sequences among various prenyltransferases, particularly on those sequences which are peculiar to medium- or long-chain prenyltransferases such as hexaprenyl diphosphate (HexPP, C30) synthetase, heptaprenyl diphosphate (HepPP, C35) (Koike-Takeshita, A. et al. (1995) J. Biol. Chem. 270:18396–18400) synthetase and octaprenyl diphosphate (OctPP, C40) (Okada, K. et al., J. Bacteriol. 179, 3058–3060 (1997)) synthetase.

Sense primers:

S1 (designed based on SEQ ID NO: 3):
5'-(CG)(AG)CGG(AT)AA(AG)C(AG)(CGT)AT(CGT)CGTCC-3'(SEQ ID NO: 14)

S2 (designed based on SEQ ID NO: 4):
5'-A(CT)(ACGT)GC(GT)(AT)C(ACGT)CT(ACGT)(CGT)T(ACGT)CACGA-3' (SEQ ID NO: 15)

S3 (designed based on SEQ ID NO: 3):
5'-GG(ACGT)GG(ACGT)AA(AG)CG(ACGT)AT(ACT)CG(ACGT)CC-3' (SEQ ID NO: 16)

S4 (designed based on SEQ ID NO: 5):
5'-GC(ACGT)TC(ACGT)CT(ACGT)CT(ACGT)CA(CT)GACGA-3' (SEQ ID NO: 17)

S5 (designed based on SEQ ID NO: 6):
5'-GC(ACGT)GA(CT)TT(AG)(AC)G(ACGT)(AC)G(ACGT)GG-3' (SEQ ID NO: 18)

S6 (designed based on SEQ ID NO: 7):
5'-(CT)T(ACGT)GC(ACGT)GG(ACGT)GA(CT)TT(CT)TT(AG)TT-3' (SEQ ID NO: 19)

Antisense primers:

A1 (designed based on SEQ ID NO: 13):
5'-(GT)T(AG)(AT)AATCGAG(TA)A(ACT)(AG)TC(AG)TC-3' (SEQ ID NO: 20)

A2 (designed based on SEQ ID NO: 8):
5'-(ACGT)A(AG)(CT)TG(CT)AA(ACGT)A(AG)(CT)TC(ACGT)CC-3' (SEQ ID NO: 21)

A3 (designed based on SEQ ID NO: 9):
5'-(AGT)AT(ACGT)AG(ACGT)AG(ACGT)GC(ACGT)GT(TC)TT-3' (SEQ ID NO: 22)

A4 (designed based on SEQ ID NO: 10):
5'-(AG)TC(AG)TC(AGT)AT(CT)AA(CT)TG(AG)AA-3' (SEQ ID NO: 23)

A5 (designed based on SEQ ID NO: 11):
5'-(AG)AA(AG)TC(ACGT)A(AG)(AGT)AT(AG)TC(AG)TC-3' (SEQ ID NO: 24)

A6 (designed based on SEQ ID NO: 12):
5'-(AG)TC(AG)TC(ACGT)CC(ACGT)AC(AG)TT(CT)TT(ACGT)CC-3' (SEQ ID NO: 25)

(3) Amplification of a Prenyltransferase Gene Fragment by PCR

A PCR was conducted using TaKaRa Taq from Takara Shuzo. Usually, the composition of the reaction mixture was as follows. As a template, the genomic DNA from *P. denitrificans* was used.

| TaKaRa Taq | 2.5 U |
|---|---|
| Tris-HCl (pH 8.3) | 10 mM |
| KCl | 50 mM |
| MgCl$_2$ | 1.5 mM |
| dNTP mixture | 0.2 mM each |
| Template | 0.1 µg |
| Primer 1 (any one of SEQ ID NOS: 14–19) | 2.5 µg |
| Primer 2 (any one of SEQ ID NOS: 20–25) | 2.5 µg |
| H$_2$O | to make 100 µl |

The PCR was conducted with DNA Thermal Cycler PJ2000 (Takara Shuzo). The PCR cycles were as described below.

Briefly, 5 cycles of denaturation at 97° C. for 30 seconds, annealing at 40° C. for 30 seconds, and extension at 70° C. for 1 minute; then 30 cycles of denaturation at 97° C. for 30 seconds, annealing at 55° C. for 30 seconds, and extension at 70° C. for 1 minute were carried out.

After completion of the PCR, the products were subjected to electrophoresis with 1×TBE/5% acrylamide gel. The amplified DNA fragments were confirmed (FIG. 4) and recovered by the gel recovery method. The DNA clone obtained by the reaction using primers S4 (SEQ ID NO: 17) and A6 (SEQ ID NO:25) was designated "pCR14". Then, pCR14 was purified and sub-cloned into pT7BlueT-vector (Novagen). The base sequence of pCR14 was determined with an automatic base sequence analyzer (ABIPRISM™ 310 Genetic Analyzer), followed by analysis using a gene analysis software GENETIX for comparison with the amino acid sequences of other prenyltransferases.

As a result, the amino acid sequence encoded by pCR14 exhibited 45.7% homology to the amino acid sequence of *E. coli* OctPP synthetase, 35.5% homology to the amino acid sequence of *B. stearothermophilus* HepPP synthetase, and 31.8% homology to the amino acid sequence of *E.coli* FPP synthetase (FIG. 5).

(4) Southern Blot Analysis

Figure 6:
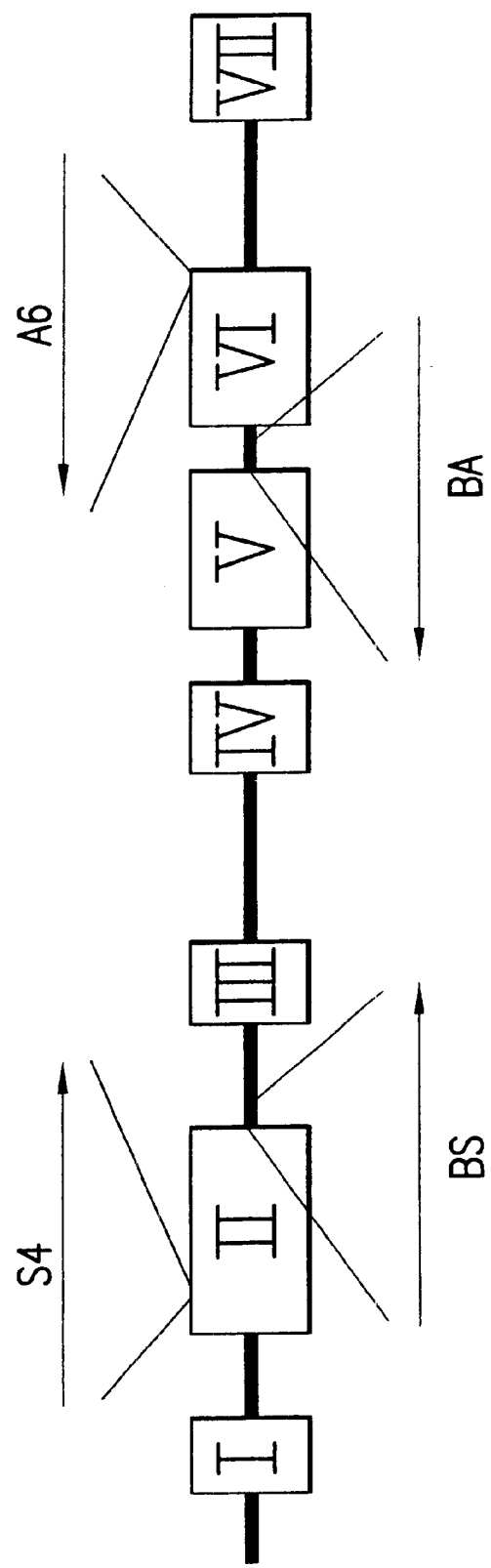
FIG. 6 is a diagram showing the design of PCR primers.

For the sub-cloned and sequenced PCR product (i.e., pCR14), PCR primers (BS and BA; FIG. 6) were newly designed based on its sequence located inside of the above-described degenerate oligo primers (S4 and A6). Using these primers, a DNA fragment to be used as a probe for hybridization was amplified by PCR and recovered.

Sense primer

BS: 5'-CCGGCCGACGCAAACCTT-3' (SEQ ID NO: 26)

Antisense primer

BA: 5'-CTGCTGCACCGCCGGGTC-3' (SEQ ID NO: 27)

The amplification was conducted 30 cycles, 1 cycle consisting of denaturation at 97° C. for 30 seconds, annealing at 55° C. for 30 seconds and extension at 72° C. for 1 minute.

Using a 300 bp fragment thus amplified as a probe, Southern blot analysis of the genomic DNA from *P. denitrificans* was performed. The PCR product was labelled with [α-$^{35}$S]dCTP (Amersham) using a commercial kit (Ready To Go DNA Labelling Beads; Pharmacia). The labelling was performed according to the protocol attached to the kit.

A filter was prepared by the following procedures. The chromosomal DNA from *P. denitrificans* (10 µg) was completely digested with ApaI, EcoRI and BamHI separately. Each of these digests was electrophoresed on 0.5×TBE/0.7% agarose gel, alkali denatured, and then transferred to a nitrocellulose membrane filter (Zeta Probe Blotting Membrane from BioRad or Hybond-N+ from Amersham).

The composition of a hybridization solution was varied as shown below depending on homology to the probe. The filter was incubated in the solution at a constant temperature of 42° C. to perform prehybridization and hybridization.

(i) Stringent conditions (homology=approx. 100%)

5×SSC

5×Denhardt's solution

1% SDS 0.2 mg/ml denatured salmon sperm DNA

50% formamide $^{35}$S-probe (this is omitted in the prehybridization)

(ii) Moderate conditions (homology=approx. 50%)

5×SSC

5×Denhardt's solution

1% SDS 0.2 mg/ml denatured salmon sperm DNA

25% formamide $^{35}$S-probe (this is omitted in the prehybridization)

Conditions for washing after the hybridization were also varied as follows.

Stringent conditions (homology=approx. 100%):

0.1% SDS, 0.1×SSC, at 68° C.

Moderate conditions (homology=approx. 50%):

0.1% SDS, 2×SSC, at 55° C.

After washing, the filter was exposed to a Fuji imaging plate and analyzed with Fuji BAS-2000 Bioimage Analyzer System.

As a result, under the stringent conditions (under which the homology between the detected bands and the primers would be approximately 100%), a 16.5 kbp band was detected when the genomic DNA had been digested with ApaI; a 18.5 kbp band was detected when the genomic DNA had been digested with EcoRI; a 11.2 kbp band and a slightly weakly hybridizing 4.2 kbp band were detected when the genomic DNA had been digested with BamHI (FIG. 7A). The slightly weak 4.2 kbp band is predicted to contain a sequence which is highly homologous to the sequences obtained this time that appear to code for a prenyltransferase gene. In other words, this 4.2 kbp band is predicted to contain another prenyltransferase gene (FPP synthetase) of *P. denitrificans*.

On the other hand, under moderate conditions (under which the homology between the detected bands and the primers would be approximately 50%), additional bands were confirmed as follows: a 7.4 kbp band when the genomic DNA had been digested with ApaI, a 5.3 kbp band when the genomic DNA had been digested with EcoRI and a 5.2 kbp band when the genomic DNA had been digested with BamHI (FIG. 7B). These bands are very likely to contain other prenyltransferase genes.

(5) Recovery of a Full Length Gene by Colony Hybridization

In order to recover a full length gene containing the gene fragment amplified by PCR, colony hybridization was conducted using the same probe as used in the Southern hybridization. First, the genomic DNA from *P. denitrificans* was partially digested with Sau3AI. Then, 5–10 kbp fragments were recovered and sub-cloned into pUC119-BamHI vector to thereby obtain 10 libraries separately each of which contained about 2000 clones. Plasmid was recovered from each library, digested with EcoRI and then subjected to Southern hybridization. Thus, those libraries which surely contained the gene of interest were selected.

Figure 8:
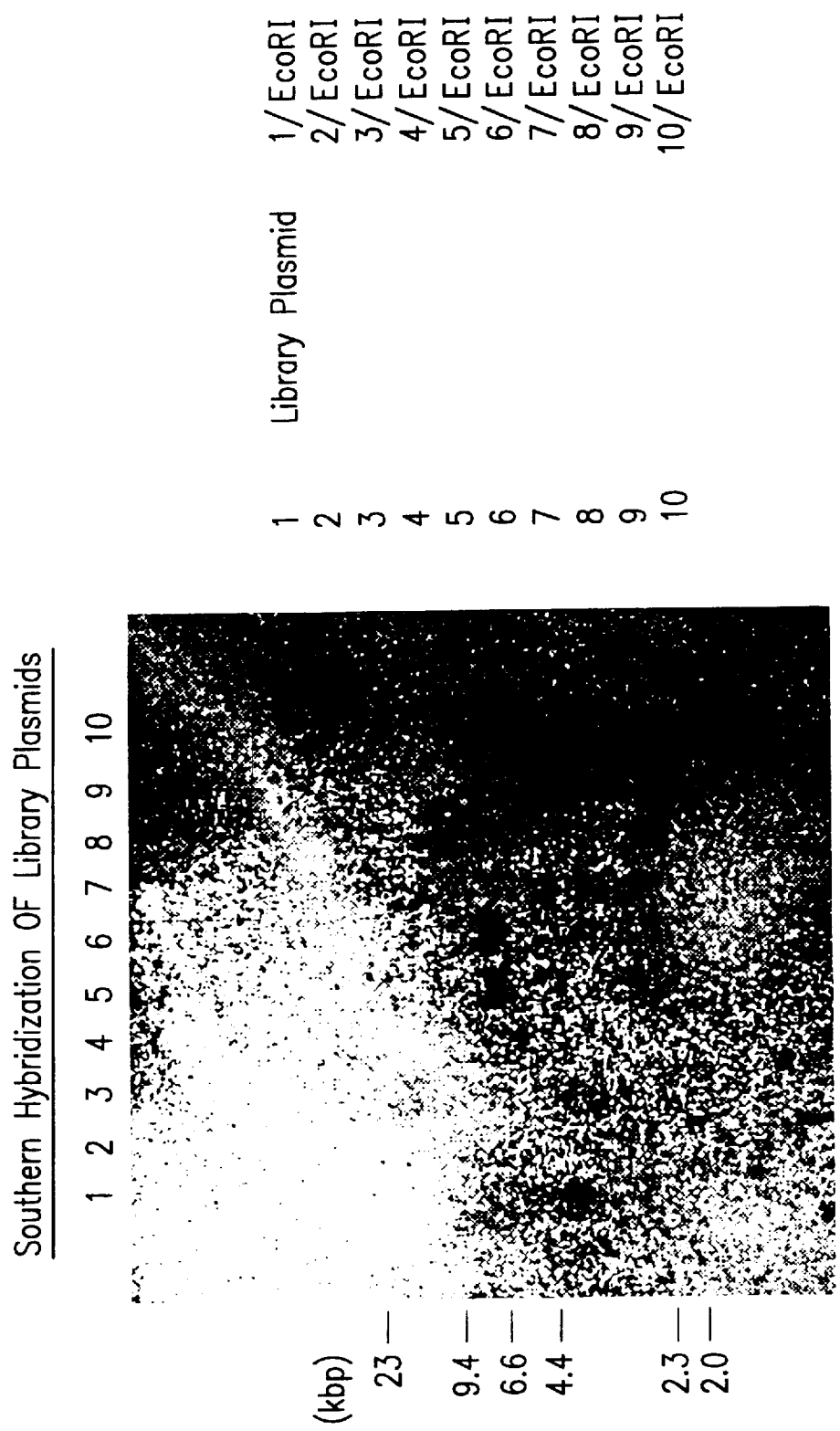
FIG. 8 is an electrophorogram showing the results of Southern hybridization.

As a result, strongly hybridizing bands were detected in libraries Nos. 9 and 10 among the 10 libraries (Nos. 1–10) (FIG. 8).

Then, library No. 10 which had exhibited the strongest bands in Southern hybridization was subjected to colony hybridization to thereby obtain 3 positive clones. Plasmids were recovered from them and designated p11A1, p11A2 and p11C1, respectively. Since each of these clones had an insert of about 7 kbp, it was confirmed by PCR if these clones contained the gene of interest.

Figure 9:
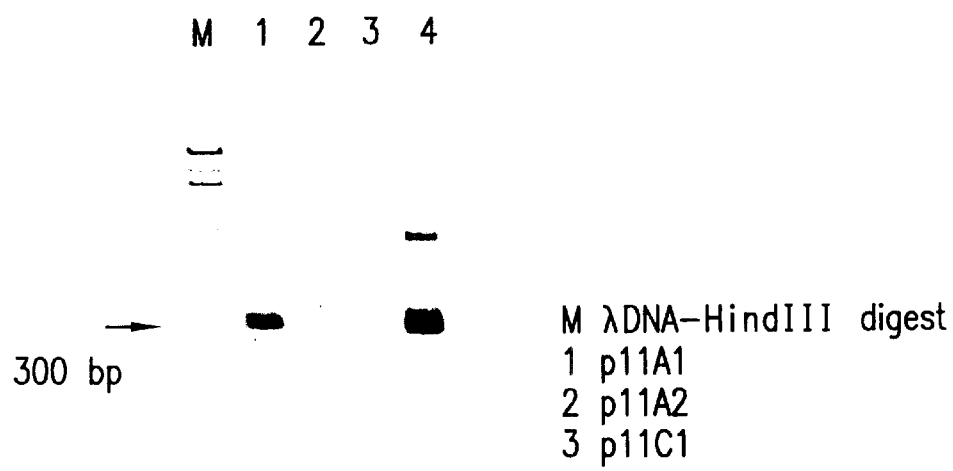
FIG. 9 is an electrophorogram showing the results of Southern hybridization.

Briefly, using PCR primers BS and BA described above, a PCR was performed with these clones and pCR14 as templates. It was observed whether a band similar to that amplified in pCR14 is also amplified in these clones (FIG. 9). The PCR was performed 25 cycles, 1 cycle consisting of denaturation at 98° C. for 30 seconds, annealing at 67° C. for 30 seconds and extension at 74° C. for 30 seconds.

As a result, only p11A1 (lane 1) exhibited amplification of a DNA fragment of about 300 bp similar to the fragment amplified in pCR14 (lane 4) (FIG. 9). No amplification was recognized in p11A2 and p11C1 under these conditions. Therefore, it is believed that they do not contain a full length gene of interest or they contain a different prenyltransferase gene.

Figure 10:
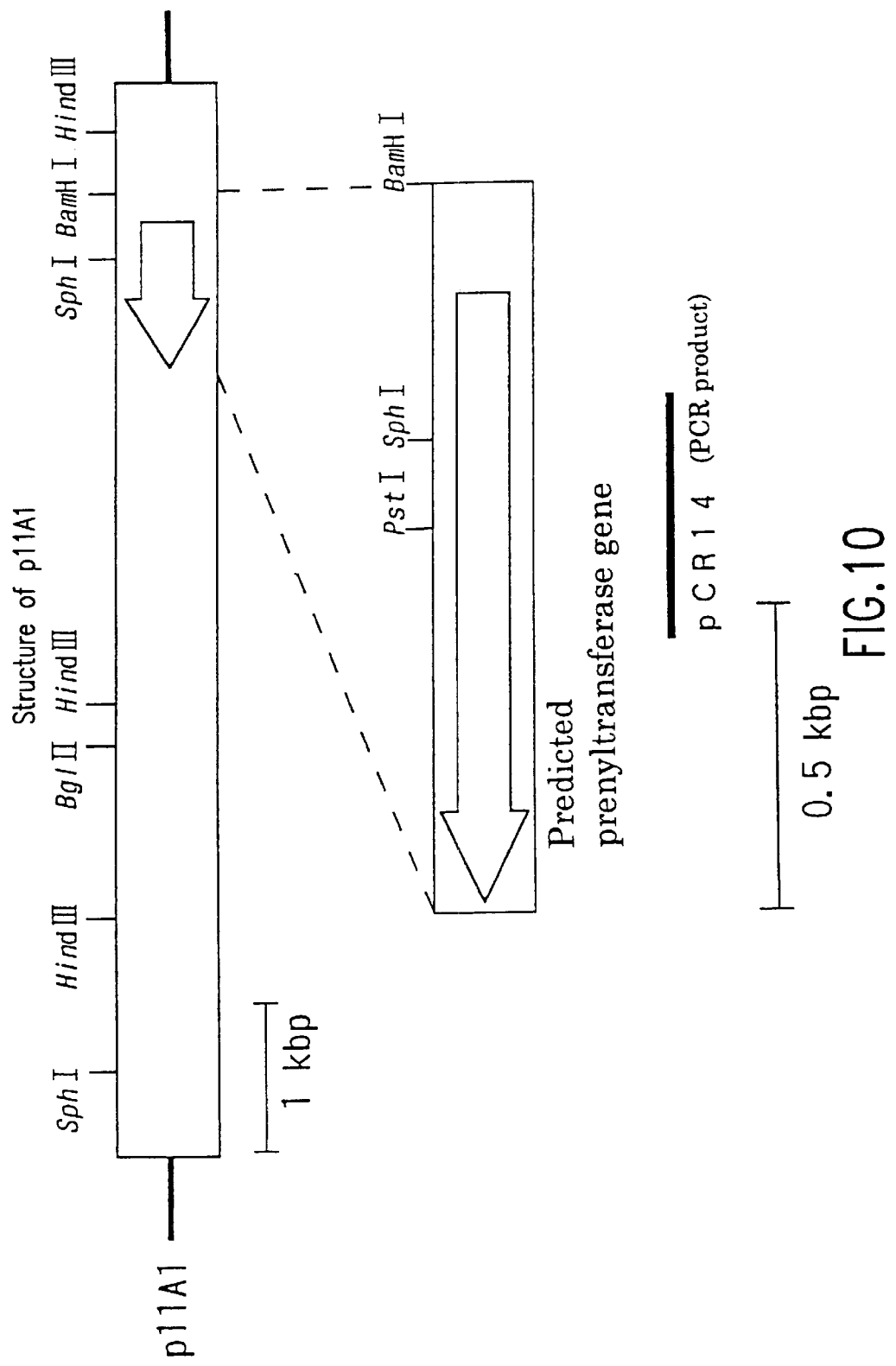
FIG. 10 is a diagram showing the structure of plasmid p11A1.

Subsequently, by preparing a restriction map for p11A1, it was ascertained where the sequence identical with pCR14 is contained in its insert of about 7 kbp (FIG. 10). Also, it was confirmed that a full length prenyltransferase gene was contained (FIG. 10). As a result, it was found that the sequence identical with pCR14 is located about 1.1–1.5 kbp from an end of the insert of p11A1. Considering that the average gene length of prenyltransferases is about 1 kbp and that the preserved Regions II to VI are contained in pCR14, the insert of p11A1 was expected to contain a full length of a prenyltransferase gene.

(6) Deletion of p11A1 and Determination of the Base Sequence

First, the present inventor decided to determine the total base sequence for the prenyltransferase gene contained in p11A1. Deletion of p11A1 was allowed to proceed from the BglII site located 4 kbp downstream of the sequence identical with pCR14, and finally, DNA fragments were cut out at the BamHI site located 430 bp upstream of pCR14. The resultant fragments were ligated to pUC119 vector digested with SmaI and BamHI.

The vectors were screened by colony hybridization. The recovered clone was cut with BglII and then digested from the 3' end with exonuclease III. The reaction was terminated after an appropriate time period. Thereafter, resultant DNA fragments were blunt-ended with mung bean nuclease or Klenow fragment. Finally, the DNA fragments were cut out by digesting with BamHI.

These fragments were electrophoresed on 3.5% acrylamide gel. Thereafter, the fragments were recovered from the gel and used to transform E. coli DH5α. Several single transformants were selected and plasmids were recovered therefrom.

These plasmids carrying a deletion product were applied to a sequencer (from ABI) to thereby determine the base sequence for the full length gene.

As a result, an ORF was found out which contains a base sequence identical with pCR14 and has in its amino acid primary sequence the 7 preserved areas peculiar to prenyltransferases (FIG. 11; SEQ ID NO: 28).

This ORF has 4 ATG codons which may be the translation initiation point. Of these, the third methionine which is close to Shine-Dalgarno consensus sequence and has a reasonable distance from it is believed to be the translation initiation point.

The amino acid primary sequence of this ORF was compared with the primary sequences of major prenyltransferases so far cloned. As a result, this ORF has 34.9% homology to E. coli FPP synthetase; 31.1% homology to B. stearothermophilus FPP synthetase; 31.8% homology to E. uredovora GGPP synthetase; 26.3% homology to M. luteus BP-26 HexPP synthetase; 34.4% homology to B. stearothermophilus HepPP synthetase; and 44.2% homology to E. coli OctPP synthetase (FIG. 12).

During the process of deletion, a downstream base sequence of about 1 kbp adjacent to the ORF of the prenyltransferase contained in p11A1 was determined.

As a result, a typical terminator sequence characterized by a repetitive sequence and repetition of T was found at 25 bp downstream of the ORF termination codon TGA (nucleotide positions from 1174 to 1201 in FIG. 11 and SEQ ID NO: 28). Therefore, it was found that there is no ORF forming an operon in the downstream of this prenyltransferase gene.

Figure 13:
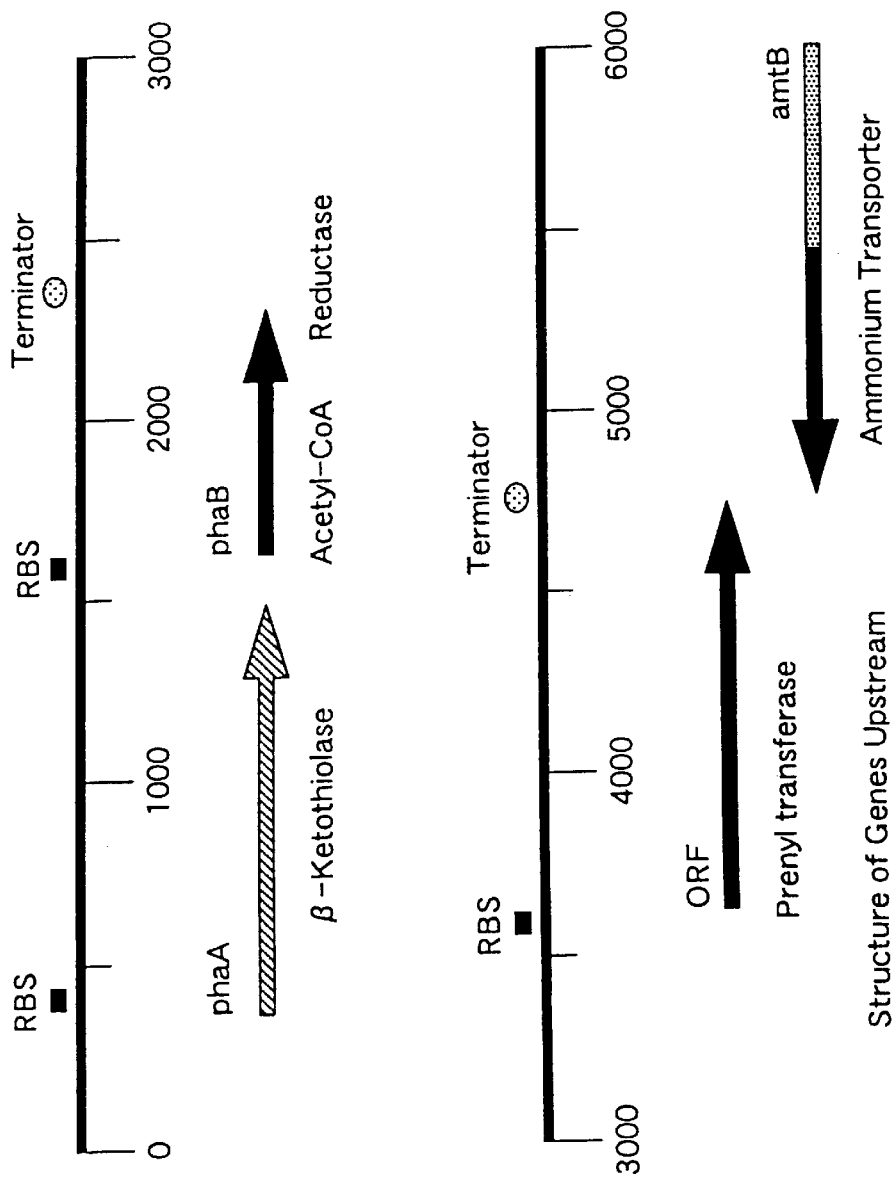
FIG. 13 is an illustrative diagram showing genes located upstream and downstream of the gene of the present invention.

Also, an upstream base sequence of about 1 kbp adjacent to the BamHI site upstream of the ORF was determined. As a result, it was found that an operon of 3.3 kpb exists in the upstream of the prenyltransferase gene, which operon is composed of the β-ketothiolase gene and acetyl-CoA reductase gene of P. denitrificans already cloned and analyzed (Yabuntani, T. et al., (1995) FEMS Microbial. Lett. 133:85–90). Although these two genes are forming an operon, the operon is terminated by a terminator. Thus, they are not forming an operon with the gene of the invention (FIG. 13).

EXAMPLE 2

Construction of a High Expression System for the Prenyltransferase

In the present invention, a system which allows compulsive expression of the prenyltransferase with a strong trc promoter and SD sequence from pTrc99A was constructed by introducing an NcoI site into the initiation codon (ATG) of the ORF and then sub-cloning it into the NcoI site of a high expression vector pTrc99A.

An expression plasmid was prepared by introducing into a plasmid an ORF which starts from an ATG methionine codon located at around the predicted position for the initiation codon based on the 7 preserved regions of known prenyltransferases.

(1) Preparation of a High Expression Plasmid

Of those ORFs which were believed to be a prenyltransferase as a result of the confirmation of base sequences, the ORF in which the third methionine is the initiation codon was introduced into the NcoI-BamHI site of the expression vector pTrc99A.

First, restriction sites were introduced into the ORF by PCR using variant oligoprimers so that the ORF could be introduced into the vector. An NcoI site (CCATGG) was introduced into the Met codon (ATG) which is the translation initiation point. Also, a BamHI site (GGATCC) was introduced into 84bp downstream of the termination codon TGA. In the introduction, primers were designed in such a manner that the amino acid immediately after the initiation codon was not changed. The sequences of the PCR primers for introducing restriction sites are as follows.

```
Sense primer                           (SEQ ID NO: 29)
DP03: 5'-ATCGCCCATGGGCATGAACGAAAACGTCTC-3'
           NcoI
```

-continued

```
Antisense primer                        (SEQ ID NO: 30)
DP13: 5'-GAGGGATCCTATAACAACTGAGGCAGCG-3'
           BamHI
```

By performing a PCR with these primers, a gene fragment having a restriction site at each end was amplified. As a polymerase for use in the PCR, KOD DNA polymerase from Toyobo was employed which is reported to be superior to Taq DNA polymerase and Pfu DNA polymerase in accuracy in DNA synthesis and amplification efficiency (Barnes, W. M. (1994) Proc. Natl. Acad. Sci. USA 91:2216–2220). The composition of the reaction mixture and the PCR cycles are as described below.

| | |
|---|---|
| KOD DNA polymerase | 2.5 U |
| Tris-HCl (pH 8.3) | 120 mM |
| KCl | 10 mM |
| $(NH_4)_2SO_4$ | 6 mM |
| $MgCl_2$ | 1 mM |
| dNTP mixture | 0.2 mM each |
| Template | 0.1 µg |
| Primer (DPO3) | 1.25 µM |
| Primer (DP13) | 1.25 µM |
| $H_2O$ | to make 50 µl |

The PCR was conducted 25 cycles, 1 cycle consisting of denaturation at 98° C. for 30 seconds, annealing at 67° C. for 30 seconds and extension at 74° C. for 30 seconds.

After completion of the PCR, the products were digested with NcoI and BamHI, electrophoresed on 0.8% agarose gel and recovered. The resultant NcoI-BamHI gene fragment was sub-cloned into the NcoI-BamHI site of pTrc99A (Amann, E. et al. (1988) Gene 69:301–305). The thus obtained expression plasmid was designated pDPm3. This plasmid was also sequenced to confirm the sequence of the vector and the junction sites.

As a result, it was confirmed that the ORF of the prenyltransferase is surely inserted into this plasmid and ligated without frameshift to the NcoI site.

Thereafter, E. coli DH5α was transformed with this expression plasmid pDPm3.

The E. coli carrying the expression plasmid pDPm3 (pDPm3/DH5α) has been deposited under the terms of the Budapest Treaty at the National Institute of Bioscience and Human-Technology, Agency of Industrial Science and Technology (1–3 Higashi 1-chome, Tsukuba City, Ibaraki Pref., Japan) on Jul. 9, 1997 under Accession No. FERM BP-6259.

(2) High Expression of the Prenyltransferase in E. coli

The E. coli transformed with the expression plasmid pDPm3 was inoculated into LB medium (1% bactotryptone, 0.5% yeast extract, 0.5% NaCl, 0.1% glucose) containing 50 µg/ml ampicillin and cultured overnight at 37° C. Subsequently, 1 ml of this culture fluid was inoculated into 100 ml of M9 nutrient medium (0.2% M9 salt, 0.2% glycerol, 0.2% yeast extract) containing 50 µg/ml ampicillin and cultured at 30° C. When the turbidity reached at $A_{600}$=0.6–0.8, isopropyl β-D-thiogalactopyranoside (IPTG) was added thereto to give a final concentration of 1 mM. Then, the cells were cultured overnight at 30 ° C.

The culture fluid was centrifuged at 4° C. at 1,000×g for 10 minutes and washed with 50 mM potassium phosphate buffer (pH 7.2). The resultant cells were suspended in a lysis buffer (50 mM potassium phosphate buffer (pH 7.2), 5 mM EDTA, 1 mM β-mercaptoethanol, 1 mM PMSF) and subjected to sonication [(ultrasound 10 sec.+ice cooling 2 min.)×10 cycles], to thereby disrupt cells. The sonication was conducted with Sonifier 250 from Branson. After disruption, the cell suspension was centrifuged at 4° C. at 15,000×g for 30 minutes, and the supernatant was collected as a crude enzyme extract.

Subsequently, prenyltransferase activity was determined as described below.

A 200 µl reaction solution shown below was prepared using an appropriate amount of the crude enzyme extract, various allylic primers and $[^{1-14}C]$IPP (54 or 57 Ci/mol; Amersham).

| | |
|---|---|
| Potassium phosphate buffer (pH 7.2) | 50 mM |
| $MgCl_2$ | 5 mM |
| β-mercaptoethanol | 10 mM |
| Triton X-100 | 0.5% |
| $[^{14}C]$ IPP (1Ci/mol) | 125 µM |
| Allylic primer | 25 µM |
| Crude Enzyme Extract | Appropriate volume |
| Total | 200 µl |

The solution was incubated at 37° C. for 1 hour to allow an enzyme reaction. Then, 200 µl of saturated aqueous NaCl solution and 1 ml of n-BuOH saturated with saturated aqueous NaCl solution were added thereto and agitated well. The resultant solution was centrifuged to extract the reaction products. 200 µl of the BuOH layer was collected, and 3 ml of Clear Sol was added thereto. Then, the enzyme activity was determined by measuring the radioactivity in the BuOH extract with a liquid scintillation counter. The enzyme activity was expressed in unit, one unit being the amount of IPP (nmol) taken into the reaction products per 1 minute.

As a result, prenyltransferase activity which is believed to be derived from a foreign gene was confirmed in the IPTG-induced, pDPm3-transformed E.coli (Table 2).

TABLE 2

| Transformant | Enzyme Activity − Triton X-100 | (× $10^{-3}$ unit) + Triton X-100 |
|---|---|---|
| DH5 α/pDPm3 | 1.27 | 0.553 |
| DH5 α/pDPm3 + IPTG | 9.05 | 54.4 |
| DH5 α/pUC119 + IPTG | 1.78 | 1.78 |

It is noted that significant transferase activity was not confirmed in E.coli which was transformed with pDPm3 but not induced with IPTG. This indicates that the expression of this prenyltransferase activity is under the strong control of the trc promoter.

(3) Analysis of the Reaction Product by Reversed Phase TLC

Subsequently, the prenyl diphosphate generated by the prenyltransferase was hydrolyzed with an acid phosphatase. The resultant hydrolysate was analyzed by reversed phase thin layer liquid chromatography (TLC). The acid phosphatase was purchased from Boehringer Mannheim. As a thin layer chromatography plate, LKC18 of Whatman Chemical Separation was used.

Briefly, a reaction was performed using the crude enzyme extract. The reaction products (prenyl diphosphates) were extracted with n-butanol (n-BuOH) and hydrolyzed with an acid phosphatase into corresponding prenols in the reaction solution the composition of which is shown below (Fujii, H. et al. (1982) Biochim. Biophys. Acta. 712:716–718).

| | |
|---|---|
| Butanol layer | 0.8 ml |
| 1 M acetate buffer (pH 4.7) | 0.57 ml |
| Methanol | 1.2 ml |
| Acid phosphatase | 2 mg |
| $H_2O$ | 0.43 ml |
| Total | 3 ml |

The hydrolysis was performed overnight at 37° C. After completion of the reaction, 1 ml of saturated aqueous NaCl solution and 3 ml of n-pentane were added thereto and agitated, to thereby extract the prenol with the pentane. The pentane layer was recovered and washed with $H_2O$. Then, the pentane extract was concentrated with a centrifugal evaporator and developed by reversed phase TLC (with LKC-18) to identify the reaction products (eluent: aceton:$H_2O$ =19:1). The positions of various prenols used as standard samples were visualized by exposure to iodine vapor. The TLC plate was exposed to a Fuji imaging plate, which was then analyzed with Fuji BAS-2000 Bioimage Analyzer to detect the positions of radioactive prenols.

Figure 14:
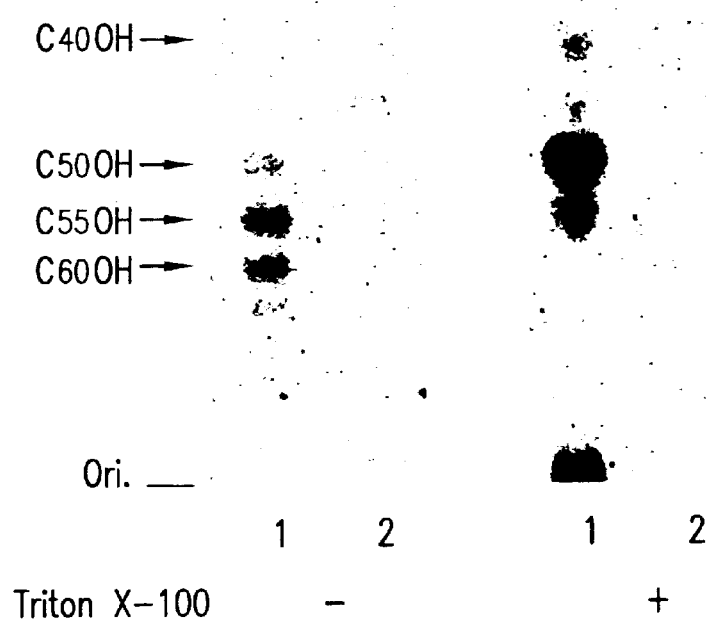
FIG. 14 provides photographs of reversed phase thin layer liquid chromatograms.

The results are shown in FIG. 14.

E. coli is known to have three prenyltransferase activities of FPP synthetase, OPP synthetase and undecaprenyl diphosphate synthetase. However, in the E. coli transformed with pDPm3, production of decaprenyl diphosphate has been confirmed (FIG. 14). Therefore, it has become clear that the gene of the invention is a DPP synthetase gene.

The substrate specificity of this DPP synthetase has been examined on various allyl primers. The unit of enzyme activity is as defined above.

As a result, this DPP synthetase exhibited the maximum activity with FPP (see Table 3; enzyme activity 54.4), though slight activity was observed with GPP. When EEE-geranylgeranyl diphosphate (trans-GGPP) or ZEE-geranylgeranyl diphosphate (cis-GGPP) was used as a substrate, strong activity was observed with trans-GGPP while little activity was observed with cis-GGPP. These results support that the enzyme of the invention is an enzyme catalyzing E-type chain elongation.

TABLE 3

Substrate Specificity of the Prenyltransferase

| Allylic Substrate | Enzyme Activity − Triton X-100 | (× $10^{-3}$ unit) Triton X-100 |
|---|---|---|
| DMAPP | 1.63 | 4.17 |
| GPP | 1.78 | 19.8 |
| EE-FPP | 9.05 | 54.4 |
| EEE-GGPP | 3.22 | 35.33 |
| ZEE-GGPP | 2.47 | 3.68 |

(4) Confirmation of High Expression of the Prenyltransferase

High expression of the prenyltransferase by means of the expression plasmid was confirmed as described below. Briefly, the crude enzyme extract was analyzed by SDS-polyacrylamide gel electrophoresis (SDS-PAGE) using RESEP GEL 12.5% (Wakamori K.K.). The positions of bands stained with Coomassie Brilliant Blue R-250 were compared with molecular markers (SDS-PAGE Molecular Weight Standards, Broad Range; BioRad).

The procedures basically followed the method of Laemmli (Laemmli U.K. (1970) Nature 227:680–685).

Figure 15:
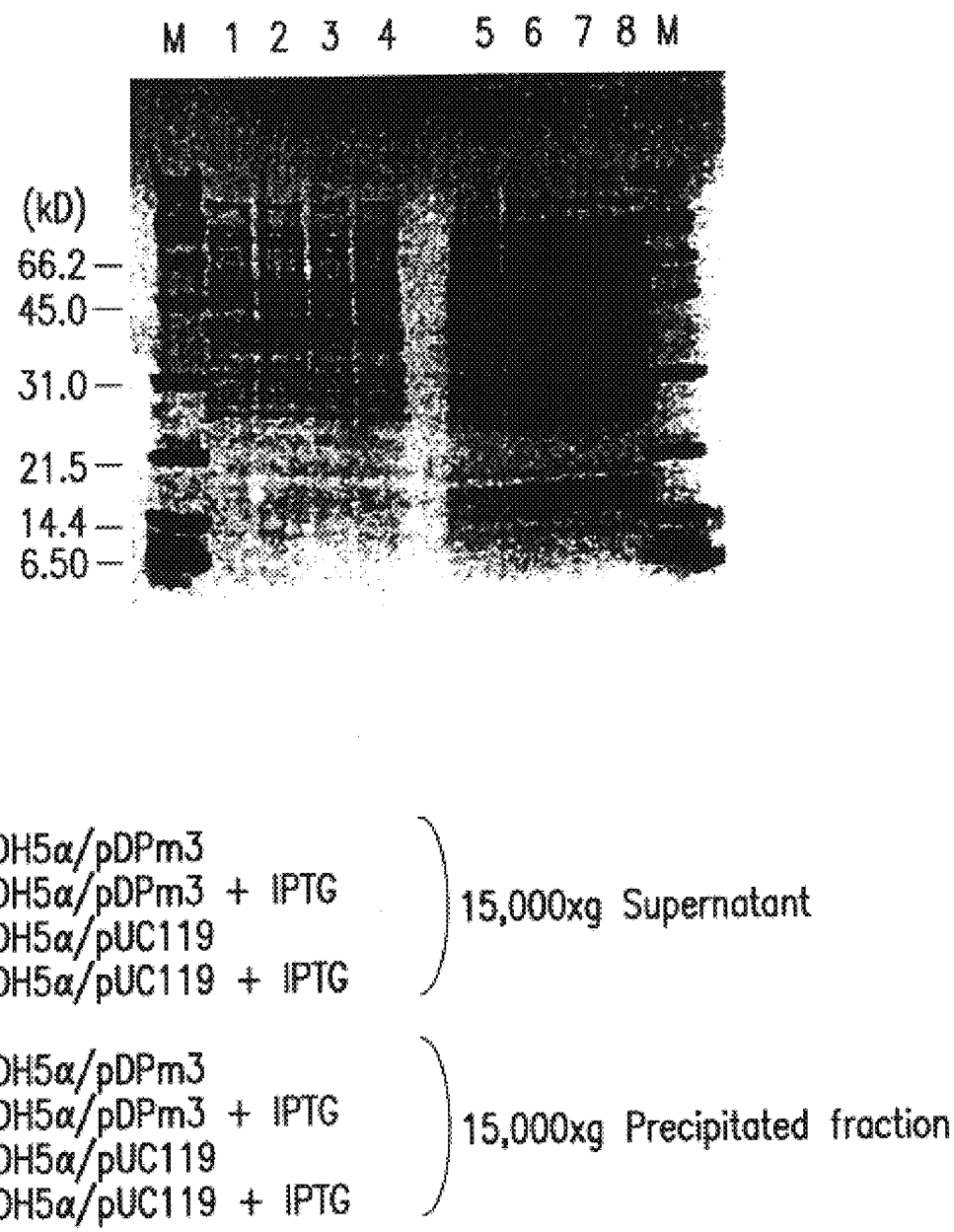
FIG. 15 is a photograph showing the results of SDS-polyacrylamide gel electrophoresis.

As a result, a band which is believed to be due to high expression was observed at around 36 kDa in the precipitated fraction after centrifugation at 15,000×g (FIG. 15, lane 6).

(5) Analysis of the Ubiquinone Side Chain Length

Ubiquinones were extracted from the E.coli transformed with pDPm3, followed by analysis of the chain length of isoprene side chains. Ubiquinone extraction was performed as described below.

First, 0.3 g of wet cells were suspended in 2 ml of methanol-0.3% NaCl solution (10:1, v/v) (hereinafter referred to as "extraction solution") and sonicated (30 min×4 times). Then, 1 ml of extraction solution was added thereto, and hexane extraction was performed twice. The extract was washed with extraction solution to remove the hexane and then dissolved in 1 ml ethanol, followed by HPLC.

HPLC equipment from Hitachi was used. As a column, LiChrosorb RP-18 (5 $\mu$m) (Merck) was used. As an eluent, EtOH (99.8%) was fed at 1 ml/min. Detection was conducted at 275 nm.

Figure 16:
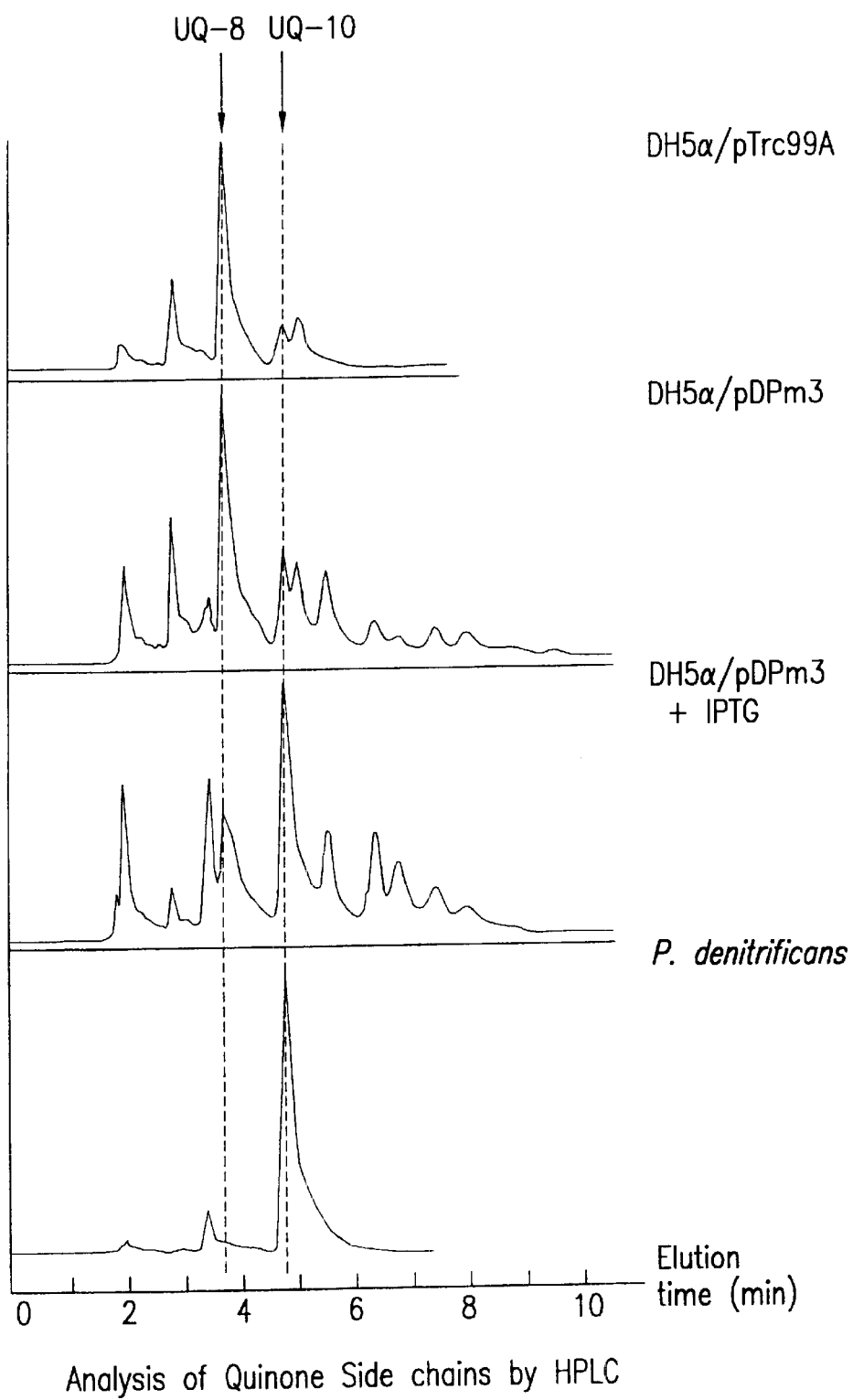
FIG. 16 provides HPLC charts showing the results of analysis of quinone side chains.

The results are shown in FIG. 16 and Table 4. In the E. coli transformed with the vector plasmid pTrc99A alone, only ubiquinone-8 (UQ-8) was detected. On the other hand, in the E.coli transformed with pDPm3, about 20% of the total ubiquinone was replaced with ubiquinone-10. Further, in the E. coli transformed with pDPm3 and cultured under induction with IPTG, about 70% of the total ubiquinone was replaced with UQ-10.

TABLE 4

| Cell | Ubiquinone Yield ($\mu$g/g wet cell) UQ-8 | UQ-10 |
|---|---|---|
| DH5 α/pUC119 | 72.7 | — |
| DH5 α/pDPm3 | 16.2 | 4.51 |
| DH5 α/pDPm3 + IPTG | 6.05 | 17.5 |
| P. denitriticans | — | 256 |

Figure 17:
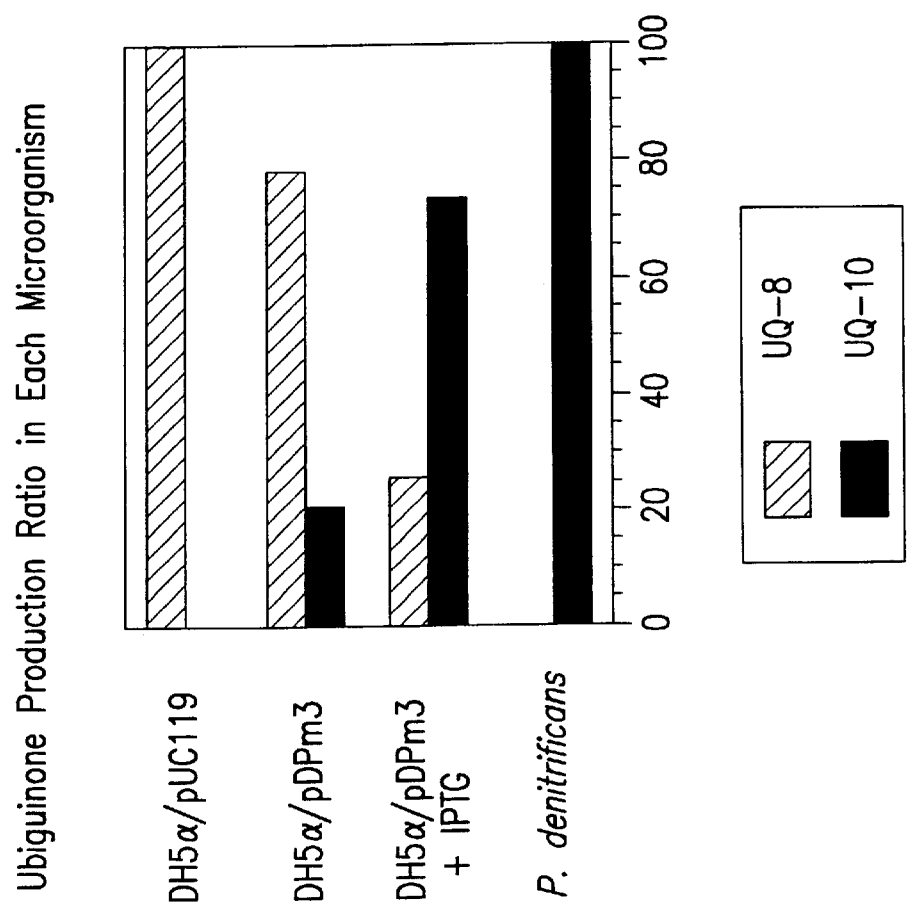
FIG. 17 is a graph showing the ratios of ubiquinone production in individual microorganisms.

From the above, it has been confirmed that the isolated gene is coding for a decaprenyl diphosphate synthetase. Although E. coli does not naturally have the ability to produce ubiquinone-10, it has become possible to allow E. coli to produce ubiquinone-10 by transforming this bacterium with this gene of the invention (FIG. 17).

EFFECT OF THE INVENTION

According to the present invention, a decaprenyl diphosphate synthetase, a gene coding for the synthetase, a recombinant vector comprising the gene, a transformant transformed with the vector, a method for producing a decaprenyl diphosphate synthetase, and a method for producing ubiquinone-10 with a transformed microorganism are provided. The enzyme and the gene of the present invention are useful for the production of the enzyme, the production of ubiquinone-10, and the like.

What is claimed is:

1. A method for producing ubiquinone-10 comprising:
(A) culturing a transformant transformed with a recombinant vector comprising
  (1) a gene coding for a recombinant protein (a) or (b) defined below:
    (a) a protein having the amino sequence of SEQ ID NO:2; or
    (b) a protein which has the amino acid sequence of SEQ ID NO:2 having deletion, substitution or addition of one amino acid and which has diphosphate synthase activity; or
  (2) a gene having the nucleotide sequence of SEQ ID NO:1; and
(B) recovering the ubiquinone-10 from the resultant culture.

2. A method for producing ubiquinone-10 comprising:
(A) culturing a transformant transformed with a recombinant vector comprising a gene having the nucleotide sequence of SEQ ID NO:1; and
(B) recovering the ubiquinone-10 from the resultant culture.

3. A method of claim 1, wherein said recovering step comprises:
  (C) lysing the resultant culture;
  (D) extracting a crude culture lysate with a solvent; and
  (E) separating the ubiquinone-10 from the resultant culture lysate.

4. A method of claim 2, wherein said recovering step comprises:
  (C) lysing the resultant culture;
  (D) extracting a crude culture lysate with a solvent; and
  (E) separating the ubiqunone-10 from the resultant culture lysate.

5. A method of claim 1, wherein said recovering step comprises:
extracting a ubiquinone-10 from the resultant culture with a solvent.

6. A method of claim 2, wherein said recovering step comprises:
extracting a ubiquinone-10 from the resultant culture with a solvent.

* * * * *

UNITED STATES PATENT AND TRADEMARK OFFICE
CERTIFICATE OF CORRECTION

PATENT NO.    : 6,410,280 B1
DATED         : June 25, 2002
INVENTOR(S)   : Obata S. et al.

It is certified that error appears in the above-identified patent and that said Letters Patent is hereby corrected as shown below:

Column 3,
Line 45, replace "10comprising" with -- 10 comprising --

Column 7,
Line 38, replace "1in a" with -- 1 in a --
Line 38, replace "also." with -- also --

Column 9,
Line 18, replace "oPP" with -- OPP --

Column 11,
Line 35, replace "pCR14exhibited" with -- pCR14 exhibited --

Column 39,
Lines 44 and 60, replace "transformant" with -- host cell --
Line 52, replace "diphosphate" with -- decaprenyl diphosphate --

Column 40,
Lines 44 and 51, replace "culture" with -- cultured cells --
Lines 47 and 54, replace "culture lysate" with -- solvent extract of (D) --

Signed and Sealed this

Fifteenth Day of July, 2003

JAMES E. ROGAN
*Director of the United States Patent and Trademark Office*